(12) United States Patent
Agemura et al.

(10) Patent No.: US 7,348,559 B2
(45) Date of Patent: *Mar. 25, 2008

(54) DEFECT INSPECTION AND CHARGED PARTICLE BEAM APPARATUS

(75) Inventors: Toshihide Agemura, Hitachinaka (JP); Mitsugu Sato, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/498,125

(22) Filed: Aug. 3, 2006

(65) Prior Publication Data

US 2006/0284087 A1    Dec. 21, 2006

Related U.S. Application Data

(63) Continuation of application No. 11/139,609, filed on May 31, 2005, now Pat. No. 7,112,792.

(30) Foreign Application Priority Data

May 31, 2004   (JP) .............................. 2004-161276

(51) Int. Cl.
    *G01N 23/00*  (2006.01)
(52) U.S. Cl. .................. 250/310; 250/309; 250/341.1; 702/84; 324/765; 438/15
(58) Field of Classification Search ..................... None
    See application file for complete search history.

(56) References Cited

U.S. PATENT DOCUMENTS 6,847,907 B1   1/2005   Novotny 7,112,792 B2 *   9/2006   Agemura et al. ............ 250/310

FOREIGN PATENT DOCUMENTS

| JP | 10-247465 | 9/1998 |
|----|-----------|--------|
| JP | 2000-348658 | 12/2000 |
| JP | 2001-15055 | 1/2001 |
| JP | 2001-283759 | 10/2001 |
| JP | 2002-52378 | 7/2002 |
| WO | WO 01/33603 | 5/2001 |

* cited by examiner

*Primary Examiner*—Jack I. Berman
*Assistant Examiner*—Zia R. Hashmi
(74) *Attorney, Agent, or Firm*—McDermott Will & Emery LLP

(57) ABSTRACT

In a defect inspection apparatus which combines a plurality of probes for measuring electric properties of a specimen including a fine circuit line pattern with a charged particle beam apparatus, the charged particle beam apparatus reduces a degradation in resolution even with an image-shift of ±75 μm or more. The defect inspection apparatus has a CAD navigation function associated with an image-shift function. The CAD navigation function uses coordinates for converting an image-shift moving amount to a DUT stage moving amount in communications between an image processing unit for processing charged particle beam images and a memory for storing information on circuit line patterns. The defect inspection provides the user with significantly improved usability.

18 Claims, 14 Drawing Sheets

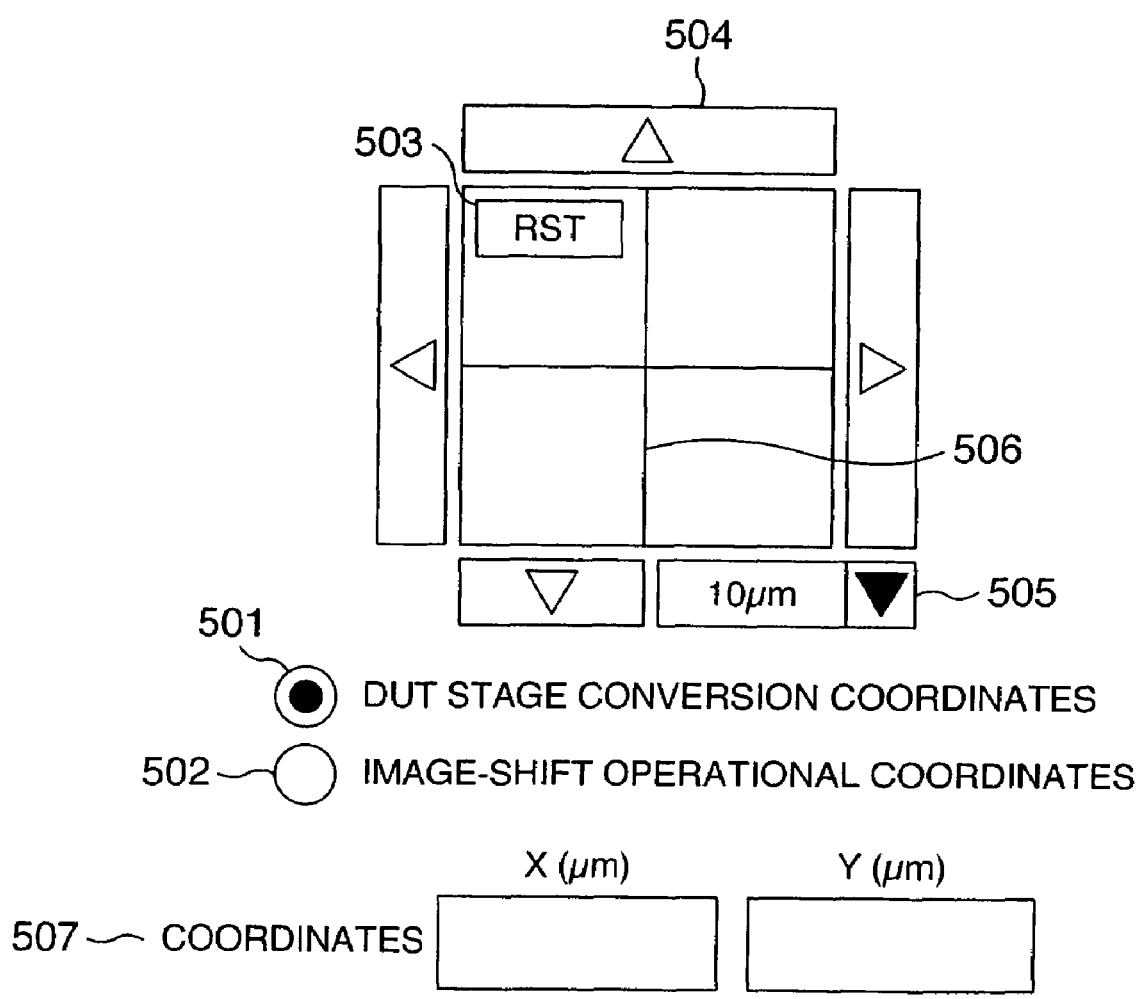

FIG.5B
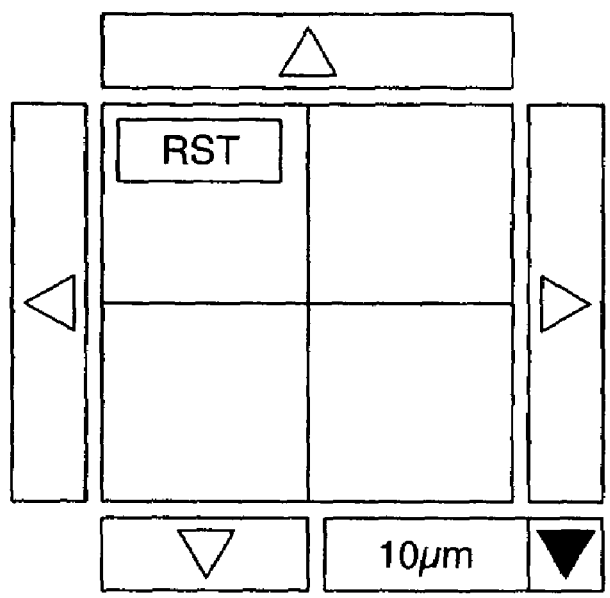
● DUT STAGE CONVERSION COORDINATES
○ IMAGE-SHIFT OPERATIONAL COORDINATES
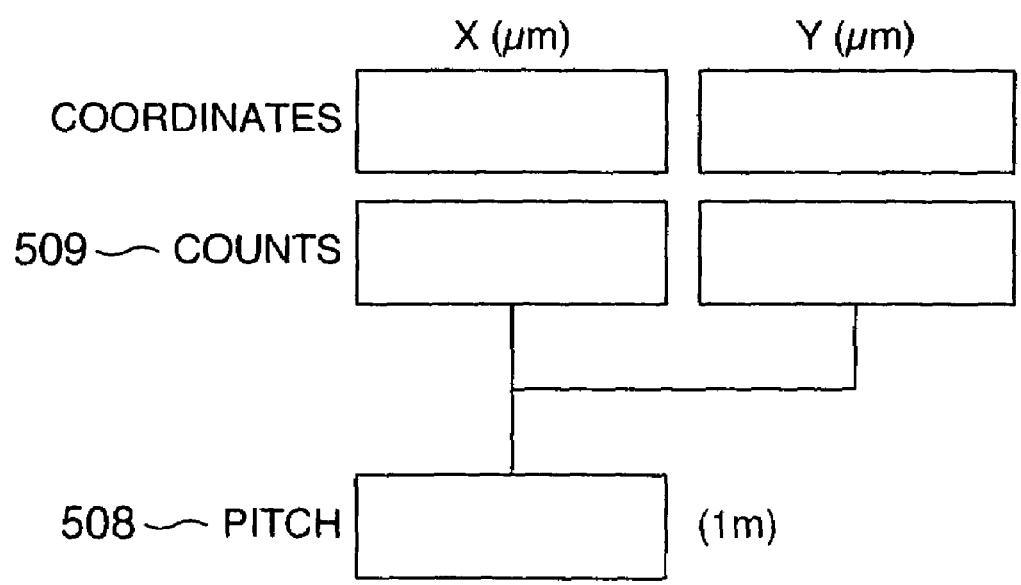

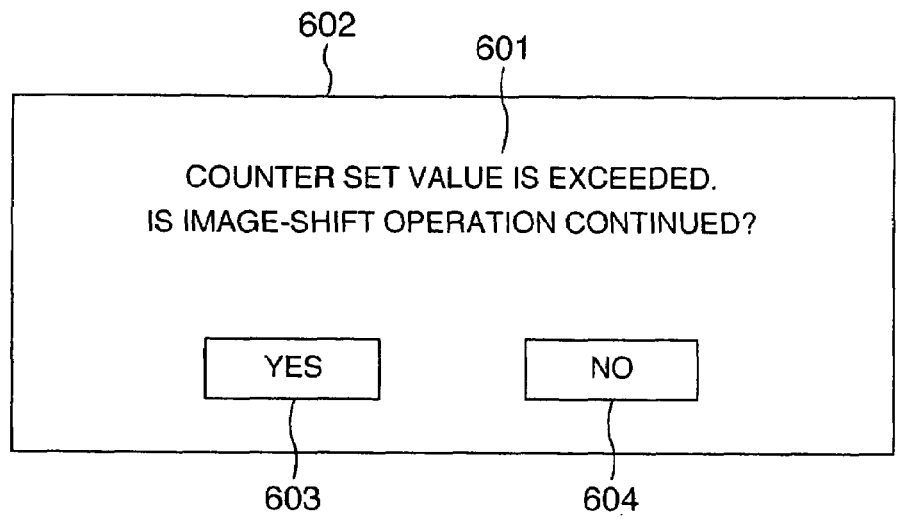
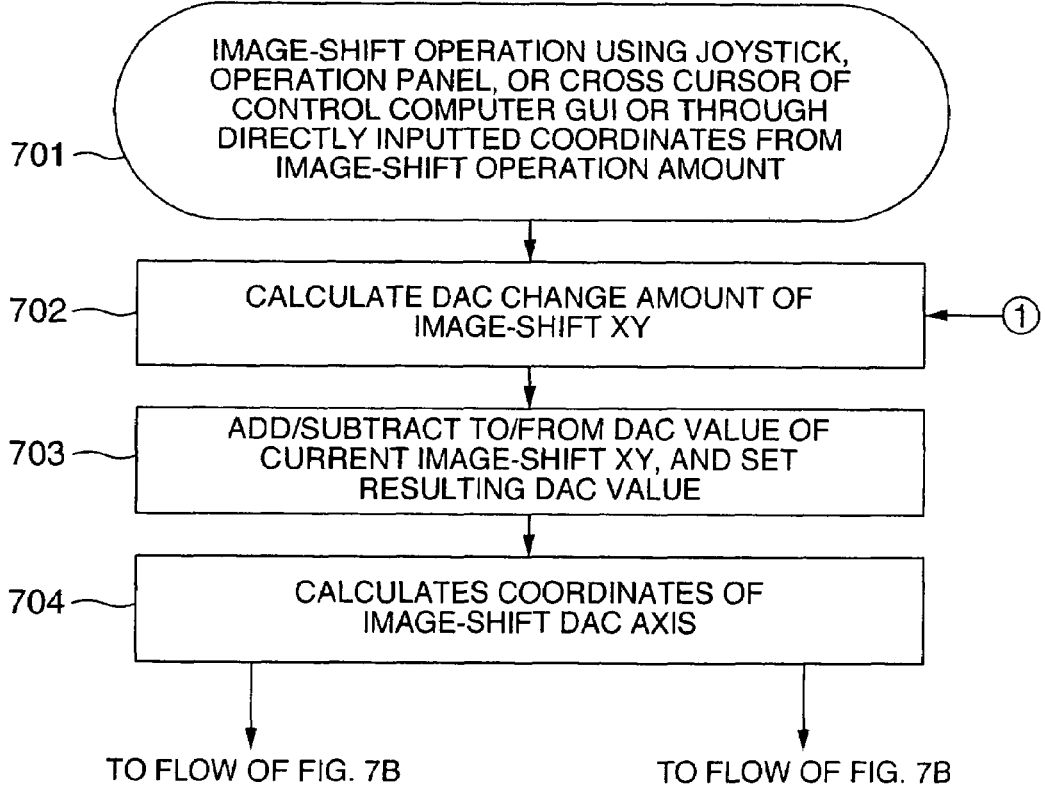

DEFECT INSPECTION AND CHARGED PARTICLE BEAM APPARATUS

This application is a Continuation of Ser. No. 11/139,609, filed May 31, 2005, now U.S. Pat. No. 7,112,792, which claims priority of Japanese Patent application No. 2004-161276, filed May 31, 2004, and the contents of which are herewith incorporated by reference.

BACKGROUND OF THE INVENTION

The present invention relates to a charged particle beam apparatus, for example, an apparatus such as a scanning electron microscope (SEM) for observing a fine pattern on a semiconductor or a general specimen, and a defect inspection apparatus for measuring electrical properties of an electronic device using a fine probe, and more particularly, to a field of view determining method for bringing a probe into contact with a specimen using an image-shift function of a charged particle beam apparatus, and a defect inspection apparatus using the field of view determining method.

Conventionally, known inspection apparatuses for detecting electrical defects in fine electronic circuits formed on semiconductor chips include inspection apparatuses such as an electron beam tester, i.e., EB tester, a probing apparatus, and the like. The EB tester is an apparatus which irradiates an electron beam onto a site under measurement, and detects electrically defective sites of an LSI, taking advantage of the fact that the amount of secondary electrons generated from a site under measurement varies depending on a voltage at the site under measurement. The probing apparatus in turn is an apparatus which brings a plurality of probes or mechanical probes, arranged to match the positions of property measuring pads of an LSI, into contact with measuring pads and plugs to measure the electrical properties of the LSI. With these EB tester and probing apparatus, an operator manually confirms a site with which a probe should be brought into contact, while viewing an image of wires such as an optical microscope (OM) image, a SEM image and the like.

In recent years, increasingly complicated circuit patterns have been formed on semiconductor devices such as LSI's, thereby making it more and more difficult to move a probe to an optimal probing position in a short time. To overcome the difficulties, a technique called "CAD navigation" displays the wiring layout of a semiconductor device in agreement with an actual image of the semiconductor device, referenced by an operator, during a probing operation to reduce a time required for the probing operation.

The SEM image is observed using a scanning electron microscope which scans a primary electron beam on a specimen or semiconductor to capture a scanned image of a fine pattern on the specimen. In order to correctly move a scan area or field of view of the primary electron beam to a point under observation on a specimen, an apparatus intended to observe a fine pattern on the specimen has an image-shift function which electrically deflects the primary electron beam to electrically move a view area in a range of several μm to approximately 10 μm using deflectors systems in series.

Also, since the image-shift function directs the primary electron beam obliquely into an objective lens, off-axis aberrations of the objective lens cause a degradation in the resolution of SEM images. To solve this problem, JP-A-10-247465, for example, discloses a technique for removing the off-axis aberrations as a function of an image-shift amount. Particularly, observations on patterned specimen such as semiconductors are generally made on the order of sub-nanometers or nanometers using low accelerating voltages equal to or lower than 5 kV in order to prevent the specimen from being charged up. When the image-shift function is used for the foregoing purposes under the foregoing conditions, it is necessary to reduce off-axis chromatic aberration and chromatic aberration associated with image-shift deflection.

When the image-shift function is not used, i.e., when the object point of an objective lens does not move, chromatic aberration of the objective lens is effectively reduced to improve the resolution by a retarding method which involves applying a negative voltage to a specimen, or by a boosting method which involves applying a positive voltage into an objective lens. On the other hand, when a specimen is irradiated with an oblique primary electron beam, i.e., in beam tilting, the primary electron beam is intentionally directed out of the axis of an objective lens to generate chromatic aberration, and the chromatic aberration is canceled out using an electrostatic and magnetic multipolar, as disclosed, for example, in JP-A-2001-15055.

While the aforementioned image-shift based movements of the field of view can be substituted by mechanical movements of a DUT stage, the image-shift function is superior in terms of the moving speed and accuracy. Even if the specimen stage (DUT) stage is improved in moving accuracy, mechanical movements cause vibrations at all times. Mechanical vibrations, if any, could damage probes because several probes are often simultaneously brought into contact with measurement plugs during a simultaneous observation in the same SEM field before other probes are brought into contact.

Thus, the operability of a defect analyzer will be significantly improved to reduce a burden on the user if the primary electron beam can be irradiated to a widest possible area, and if the CAD navigation function can be associated with the image-shift function which reduces chromatic aberration.

SUMMARY OF THE INVENTION

In recent years, increasingly complicated circuit patterns have been formed on semiconductor devices such as LSI's, thereby making it more and more difficult to move a probe to an optimal probing position in a short time, and the CAD navigation is effective for quick movements of a probe to an optimal proving position, as has been described above. However, the current CAD navigation only takes into consideration the driving of a DUT stage. The image-shift function is essential to prevent damages of probes due to mechanical vibrations of the DUT stage as mentioned above to accomplish high-speed and accurate movements of the field of view. However, there is no disclosed technique on the CAD navigation linked to the image-shift function.

It is not practically feasible to completely replace a DUT stage driving range by the image-shift. However, a need exists for a widest possible area irradiated with the primary electron beam. As will be described in detail later in connection with embodiments, for example, considering from a sector width of a current semiconductor memory mat, ±75 μm or more is required for an image-shift movement amount, while 150 μm or more is required for a total movement range. Further the size of plugs is required to be equal to or less than 200 nm, and observations should be made at a high resolution of at least 10 k or higher of SEM magnification.

The apparatus disclosed in JP-A-10-247465 can remove off-axis aberration due to a primary electron beam obliquely incident on an objective lens to provide high-resolution SEM images even with an image-shift amount five times as much as the conventional image-shift amount of several μm to approximately 10 μm. However, it is chromatic aberration due to deflection which is prominent with an image-shift of ±75 μm or more, but JP-A-10-247465 does not take into consideration the deflected chromatic aberration.

Even when the image-shift is used, the chromatic aberration can be reduced by the retarding method or boosting method. However, the retarding method involves applying a specimen with a voltage of −1 k volts or higher. In a defect inspection apparatus, probes are directly brought into contact with plugs for electric measurements, so that a voltage applied to a specimen will cause damages of not only the probes and plugs but also an overall device due to a discharge.

The image-shift is similar to the beam tilting, which has been used in recent years for three-dimensional observations on fine patterns of semiconductor devices, in that a primary electron beam is directed obliquely onto a specimen. The apparatus disclosed in JP-2001-15055 intentionally directs a primary electron beam out of the axis of an objective lens to generate chromatic aberration, and also uses an electrostatic and magnetic multipolar to generate chromatic aberration which has the same magnitude as but a different direction from the former chromatic aberration to cancel out the chromatic aberration, so that SEM images can be provided at a high resolution even under a low accelerating voltage condition which involves a large beam inclination. Further, the primary electron beam is controlled to be deflected at all times about an object point on the optical axis of the objective lens in order to minimize the off-axis aberration of the objective lens. However, the field cannot be moved unless the object point is displaced, but a movement of the object point will result in increased off-axis aberration of the objective lens. Thus, the image-shift is essentially different from the beam tilting.

In the present invention, the ratio of an object point of an objective lens to an inclination of a primary electron beam at an image point is defined as the "objective lens axis." The objective lens axis may be exemplified by a current center axis which is generally known by users of charged particle beam apparatuses. The objective lens axis, as referred to in the present invention, does not exist in the beam tilting since the object point is at center in the beam tilting.

It is therefore an object of the present invention to provide a charged particle beam apparatus which accomplishes an objective lens axis with a reduced degradation in the resolution due to chromatic aberration even with an image-shift of ±75 μm or more, and a defect inspection apparatus which has a CAD navigation function associated with an image-shift function.

The present invention relates to a technique that the coordinate user for using the coordinates for converting an image-shift moving amount to a specimen stage (DUT stage) moving amount in communications between an image processor for processing charged particle beam images and a memory for storing information on circuit line pattern, is introduced into the CAD navigation function, in the defect inspection apparatus which combines probes with a charged particle beam apparatus.

For example, as to a defect inspection apparatus for measuring electric properties of a specimen having a fine circuit line pattern formed on a wafer, wherein a charged particle beam apparatus includes a plurality of probes configured to be brought into contact with a plurality of pads connected to the circuit line pattern or with plugs to measure electric properties of the specimen, means for irradiating the specimen with a charged particle beam, image-shift means for moving a spot irradiated with the charged particle beam on the specimen, means for detecting a secondary charged particle beam generated from the specimen by irradiating the specimen with the charged particle beam to capture an image of the specimen, display means for displaying the image, input means for specifying an arbitrary location on the image, storing means for storing information on the circuit line pattern, image processing means for processing the captured image for displaying the image on the display means, and communication means for interconnecting the storing means and the image processing means, wherein the defect inspection apparatus displays the circuit line pattern and the captured image on the display means, displays information for requesting a user to specify the same location on the circuit line pattern and on the captured image, and communicates information on coordinates of a specified position between the storing means and the image processing means, and the coordinate information includes positional information of the charged particle beam on the specimen by the image-shift means, thereby achieving the aforementioned object.

The present invention significantly improves the user's convenience. Specifically, the present invention can provide a charged particle beam apparatus which reduces a degradation in resolution even with an image-shift of ±75 μm or more, and a defect inspection apparatus which has a CAD navigation function associated with an image-shift function.

Other objects, features and advantages of the invention will become apparent from the following description of the embodiments of the invention taken in conjunction with the accompanying drawings.

BRIEF DESCRIPTION OF THE DRAWINGS

FIGS. 5A to 5C are diagrams each illustrating a GUI for an image-shift unit of the PC for controlling the SEM of the defect inspection apparatus;

FIG. 6 shows an exemplary message which is displayed when an image-shift operation amount exceeds a set value;

FIGS. 7A and 7B are flow charts illustrating in combination a basic flow of image-shift control in the defect inspection apparatus illustrated in FIG. 1;

DETAILED DESCRIPTION OF THE EMBODIMENTS

Figure 1:
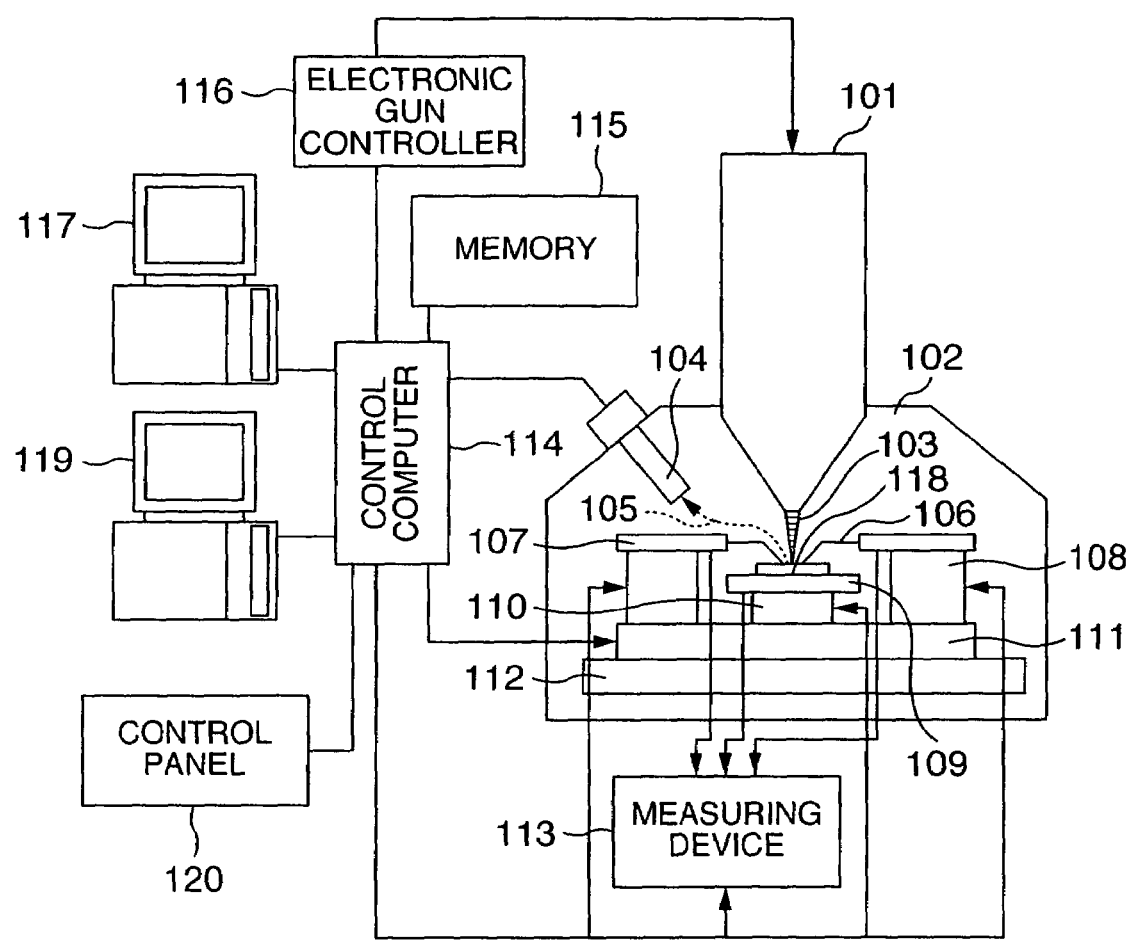
FIG. 1 is a vertically sectional view illustrating an exemplary configuration of a defect inspection apparatus.
Figure 2:
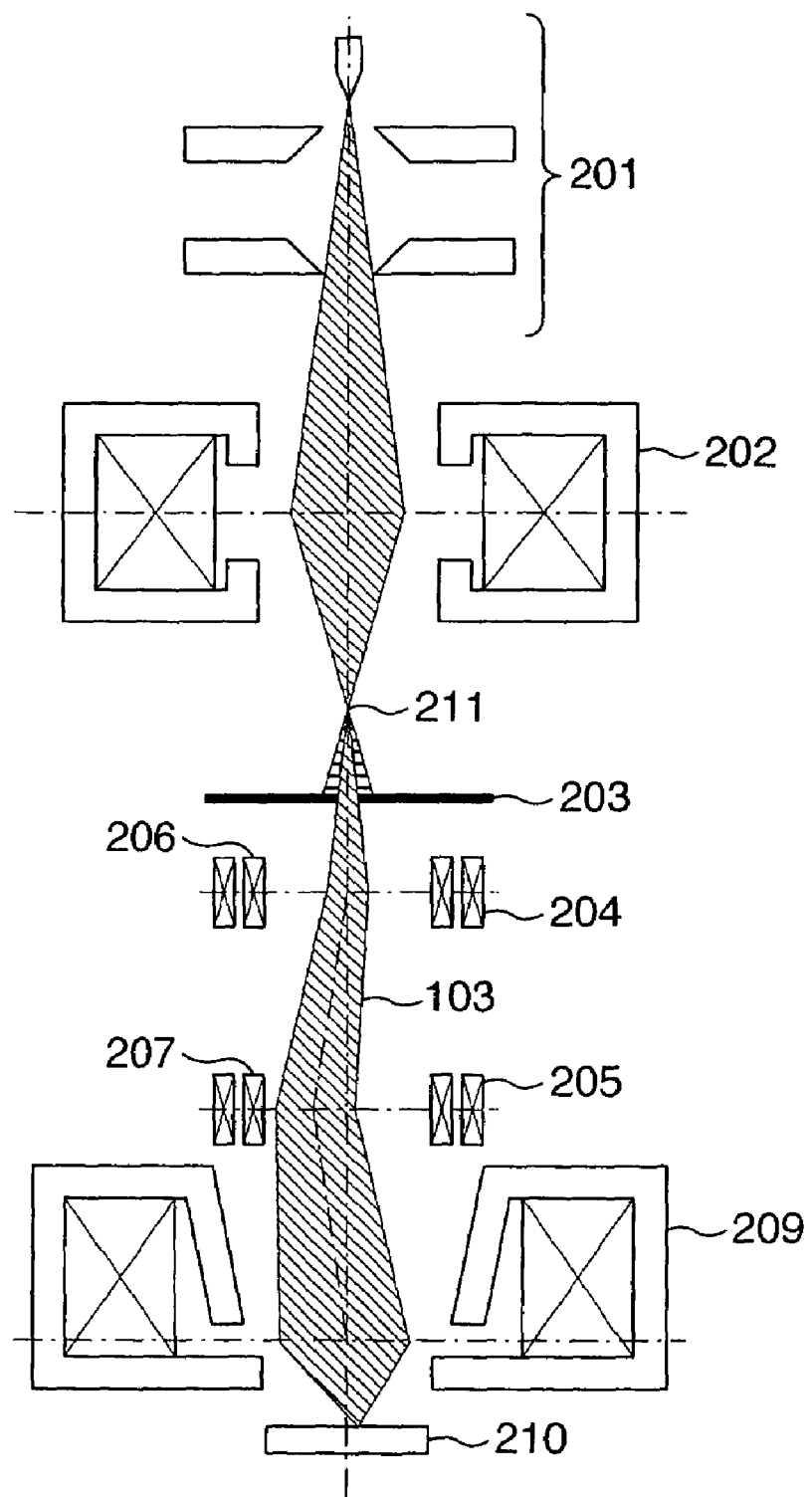
FIG. 2 is a schematic diagram illustrating in detail electron optics elements in the defect inspection apparatus illustrated in FIG. 1.

In the following, one embodiment of the present invention will be described with reference to the accompanying drawings. FIG. 1 illustrates an exemplary configuration of a defect inspection apparatus, and FIG. 2 illustrates an exemplary configuration of a scanning electron microscope (hereinafter called the "SEM"). First, the configuration of the defect inspection apparatus will be described with reference to FIG. 1.

SEM electron optics elements, generally designated by 101, make up an illumination optical system for irradiating a primary electron beam 103 onto a specimen and scanning the primary electron beam 103 on the specimen. Therefore, an electron gun 101 in this embodiment means a system which includes all components required for the SEM, such as an electron source for generating electron beams, a deflector for scanning a beam, lenses for focusing an electron beam, and the like. A vacuum chamber partition 102 separates an atmospheric area from a vacuum area. The operation of the SEM electron optics elements 101, for example, an electron beam extracting voltage for the electron source, currents applied to the deflector and lenses, and the like are controlled by an electron optics controller 116.

Secondary electrons 105 generated from a specimen 118 under inspection irradiated with the primary electron beam 103 are detected by a secondary electron detector 104. The secondary electron detector 104 comprises a sensor unit disposed within the partition 102 for actually detecting electrons, and a base unit projected out of the partition 102, to which wires are connected for connection to a power supply. A mechanical probe 106 is held by an attachment 107, and is brought into contact with a predetermined region of a specimen under inspection. A probe driving means 108, for moving the attachment 107 to a desired position, moves the mechanical probe 106 together with the attachment 107 to a desired position.

A specimen, which is actually subjected to a defect inspection, is held on a specimen holder 109. The specimen holder 109 in turn is held by a specimen holder driving means 110. The specimen holder 109 and specimen holder driving means 110 are collectively called the "DUT stage." The DUT stage and probe driving means 108 are formed on a base stage 111 which comprises a driving means for integrally driving the DUT stage and probe driving means 108 in X and Y (in-plane), and Z (vertical) directions. The integral formation of the DUT stage and probe driving means 108 on the base stage 111 is one feature of this embodiment. An important aspect, from a viewpoint of technical idea, is to configure the apparatus such that both the specimen 118 under inspection and mechanical probe 106 can be moved independently of each other as well as integrally with each other. The base stage 111 is further carried on a base 112.

The specimen holder 109 and attachment 107 are connected to an electrical property measuring device 113. The electrical property measuring device 113 mainly measures the current-voltage property of a specimen detected by the mechanical probe 106, to calculate a desired property value from the measured property, for example, a resistance, a current value, a voltage, and the like at a location of the specimen in contact with the mechanical probe 106. For use in analyses on semiconductor wafers, a semiconductor parameter analyzer may be used, by way of example, for the electrical property measuring device 113. The electrical property measuring device 113 is connected to the specimen base 109 because a power supply plug may be provided on a specimen carrying surface of the specimen holder 109 for applying a current or a voltage to the specimen.

The property value measured by the electrical property measuring device 113 is transmitted to a control computer 114 through a transmission line. The control computer 114 makes a higher analysis based on the information transmitted thereto. For example, the control computer 114 analyzes the measured value to determine whether a measured site is defective or normal. The control computer 114 is provided with a storing means such as an optical disk drive, a hard disk drive, a memory or the like, so that the measured electrical property value can be stored in the storing means. The control computer 114 also serves to control the operation of the overall defect inspection apparatus. For example, the electronic gun controller 116, secondary electron detector 104, probe driving means 108, specimen unit, and base stage 111 operate under the control of the control computer 114.

For the purposes mentioned above, the control computer 114 comprises a memory 115 for storing software for controlling each of components connected to the control computer 114, and an input means for the user to enter set parameters for the defect inspection apparatus. The input means may be, for example, a keyboard, a mouse for moving a pointer on an operation screen, and the like. Data on the wiring layout of a specimen under inspection (hereinafter called the "CAD image data") is stored in CAD workstation (WS) 110. The CAD WS 117 comprises an image display means for displaying a wiring layout. The CAD WS 117 is connected to the control computer 114, and transmits, as required, CAD image data to the control computer 114.

A SEM control personal computer (PC) 119 controls optical conditions, magnification, focusing, and image-shift for the SEM, the brightness of SEM images, scan speed, alignment, recording of images, movements of the stage and/or probe, and the like in response to operations performed on and commands entered through a graphical user interface (hereinafter called the "GUI") of the PC or WS. A control panel 120 implements some of functions of the SEM control PC 119, mechanical probe 106, specimen unit, and base stage 111 through operations with knobs, joystick, buttons and the like. It will be apparent that the SEM control PC 119 may be embodied in a work station.

Referring next to FIG. 2, there is illustrated an exemplary configuration of the SEM electron optics elements. A primary electron beam 208 emitted and accelerated by an electron gun 201 is focused by a condenser lens 202 in front of an aperture 203. The amount of the primary electron beam 208 passing through the aperture 203 can be adjusted by controlling the position at which the primary electron beam 208 is focused by the condenser lens 202. The primary electron beam 208, which has passed through the aperture 203, receives a deflecting action applied by image-shift coils 204, 205 and passes through an objective lens 209, and is irradiated onto a specimen 210. The image-shift coils 204, 205 may be operated independently of each other, or operated with a constant deflection ratio of the upper and lower image-shift coils. In any case, the primary electron beam 208 can be irradiated to the specimen 210 at a different position by adjusting the image-shift coils 204, 205. This operation is generally called a "beam shift" or "image-shift." Alignment coils 206, 207 are normally adjusted to pass the primary electron beam 208 through a desired axis of the objective lens 209. Also, during an image-shift operation, the alignment coils 206, 207 can adjust an object point 211 of the objective lens 209 to correct a field offset during the image-shift operation. This corrective operation will be described later in greater detail.

FIG. 2 merely illustrates an exemplary configuration of the SEM electron optics elements. For example, a second condenser lens may be inserted for controlling a convergence angle of the primary electron beam 207 on the specimen 206 after it has passed through the aperture 203. Also, while the secondary electron detector 104 is mounted on the vacuum chamber partition 102 in FIG. 1, a filter and a secondary electron detector may be disposed above the objective lens to extract and detect secondary electrons in a direction opposite to the direction in which the primary electron beam 207 travels. Further, a boosting electrode may be arranged along the optical axis for improving the resolution.

Figure 3:
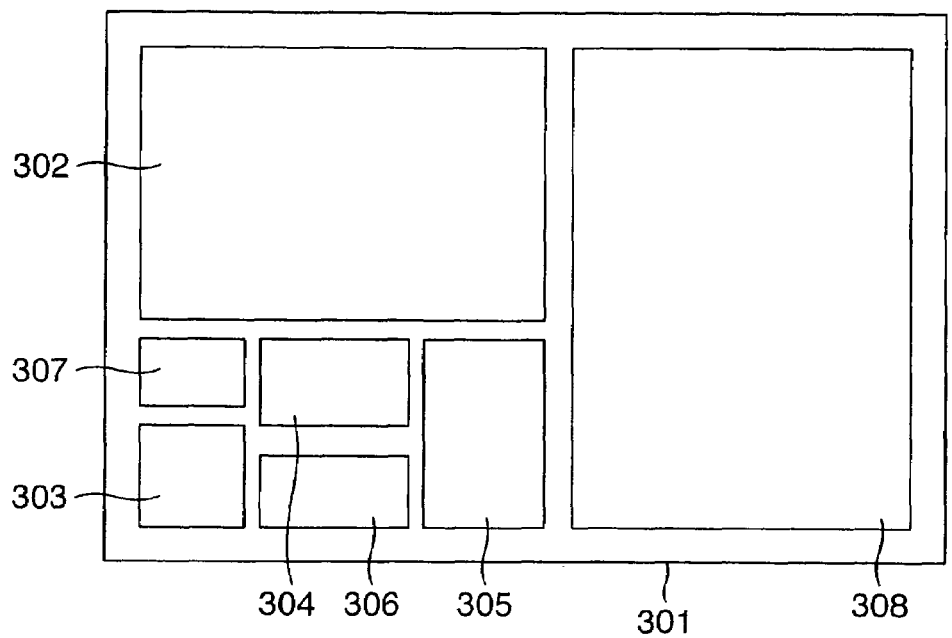
FIG. 3 is a schematic diagram illustrating a graphical user interface (GUI) associated with a personal computer (PC) for controlling a SEM of the defect inspection apparatus.

Referring next to FIG. 3, description will be made on an exemplary graphical user interface (GUI) displayed on the SEM control PC 119 of the defect inspection apparatus illustrated in FIG. 1. The GUI 301 on the SEM control PC 119 is mainly composed of seven windows. A SEM control GUI window 302 contains icons or a menu of SEM image display, settings of optical conditions for the SEM, magnification of the SEM, focus, image-shift, brightness of SEM images, scan speed, alignment, image recording, and the like. A base stage control GUI window 303 contains an icon for moving the base stage 111 to a central position, a CCD observation position, a position at which the mechanical probe 106 is exchanged, and the like, an icon for removing backlash, and coordinate input/display boxes. A DUT stage control GUI window 304 contains a cross cursor indicative of a location to which a probe is moved, an arrow-shaped icon, a combo-box for selecting a moving amount, and coordinate input/display boxes. An image-shift control GUI window 305 contains a cross cursor indicative of a location to which a probe is moved, an arrow-shaped icon, a combo-box for selecting a moving amount, coordinate input/display boxes, and a reset button for returning to an image-shift midpoint, and the like. A coordinate memory display GUI window 306 contains an icon for registering the base stage coordinates, DUT stage coordinates, and image-shift coordinates in the memory, a combo-box for selecting and calling registered coordinates, and registered coordinate display boxes. A movement selection GUI window 307 contains an icon for selecting any of the base stage, DUT stage, and shifted image for movement, and a lock icon for preventing any of the base stage, DUT stage, and shifted image from moving. Assume that the foregoing GUI windows are combined into a SEM-stage control GUI complex.

A probe control GUI window 308 for controlling the driving of the mechanical probe 106 contains an icon for selecting and displaying a probe unit which the user wishes to drive; an icon for fully retracting a probe; a scroll bar and arrow-shaped icons for driving probes X, Y, Z using a mouse; a scroll bar for finely adjusting a probe driven in the Z-direction with the mouse; reset icons for returning probes X, Y, Z to their respective midpoints; a combo-box for selecting micromotion moving speeds for the probes X, Y, Z; a combo-box for selecting increments for the probes X, Y, Z; a combo-box for selecting a continuous moving speed for the probes X, Y, Z; and a driving state display section for each probe. The probe control GUI window 308 substantially occupies the right half of the GUI 301 on the SEM control PC 119 because a large scroll bar is displayed on the GUI in order to improve the accuracy of operations on the scroll bar through the mouse for driving the probes X, Y, Z.

In FIG. 3, the SEM-stage control GUI complex is displayed on the left side of the GUI, while the probe control GUI window 308 is displayed on the right side, but the SEM-stage control GUI complex and the probe control GUI window 308 may be interchanged in place therebetween if such a change facilitates the user's observation and operations.

Figure 4A:
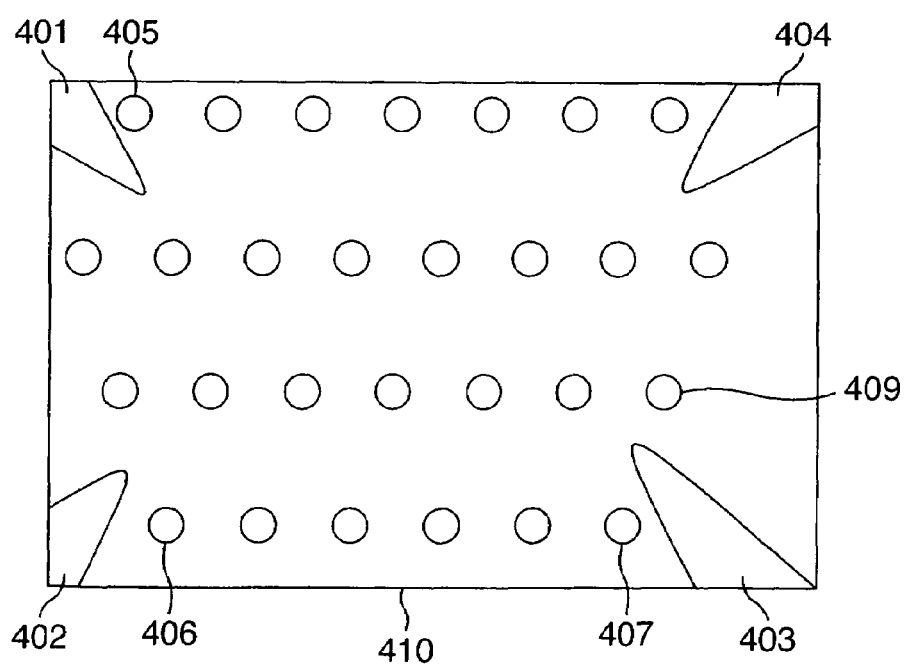
FIGS. 4A to 4C are diagrams each illustrating an exemplary SEM screen on the PC for controlling the SEM of the defect inspection apparatus.
Figure 4B:
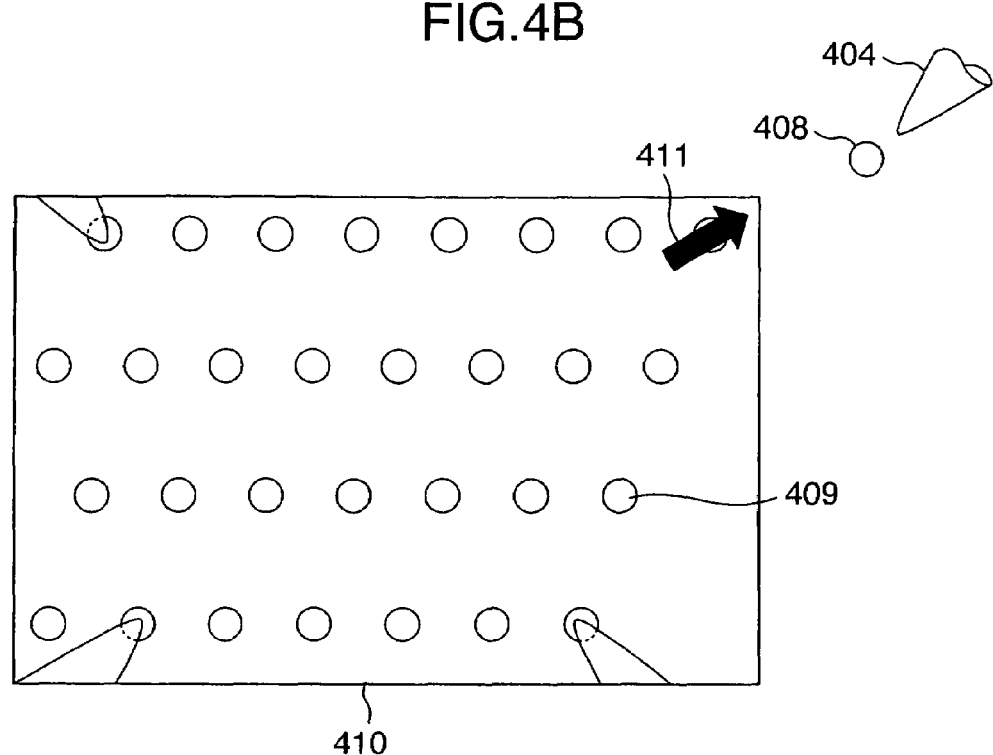
Figure 4C:
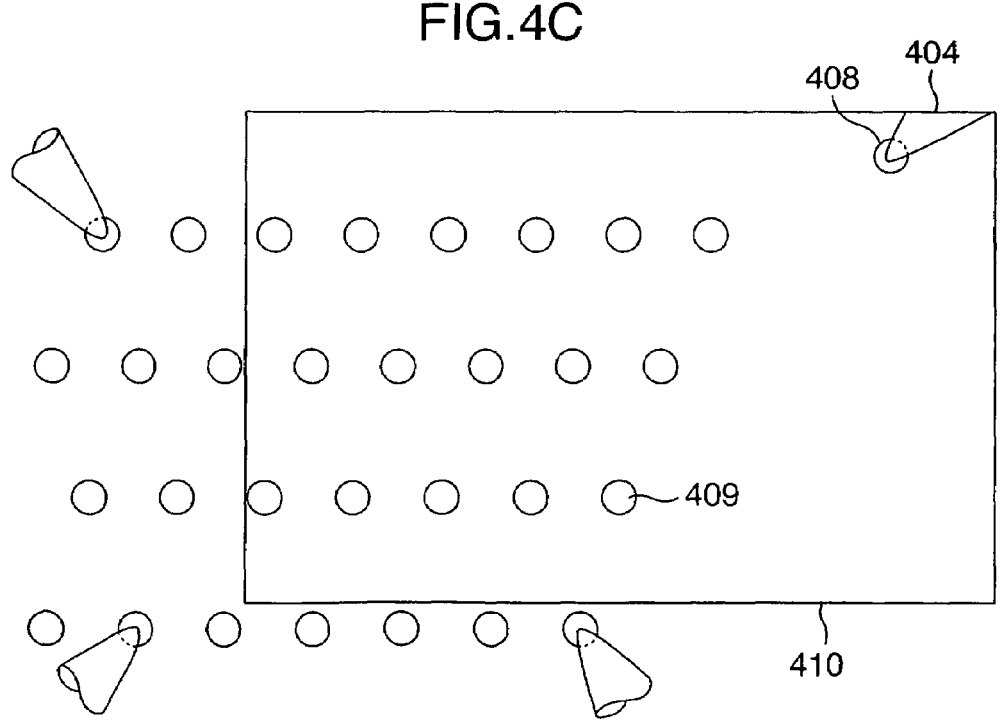

FIGS. 4A, 4B, 4C illustrate examples of SEM images displayed on the SEM control GUI window 302. In the example illustrated in FIG. 4A, when four probes are used to conduct a defect inspection, four probes are included in the SEM screen field. The probe unit is operated such that a probe 401 is brought into contact with a target plug 405 of a plurality of plugs 409, and a probe 402 is brought into contact with a target plug 406. A probe 403 has already been in contact with a target plug 407. A probe 404 is brought into contact with a target plug out of the SEM field 410. In the situation illustrated in FIG. 4A, the SEM field 410 includes the three probes which should be brought into contact with target plugs, in which case the stage need not be moved, or no image-shift operation is required.

In the example illustrated in FIG. 4B, three probes have already been in contact with their respective target plugs. However, a target gate plug 408 associated with the probe 404 is out of the SEM field 410. In this event, the stage cannot be moved because of mechanical vibrations possibly associated therewith, which could damage the probes in contact. While the stage may be slowly moved in order to prevent damages of the probes, the probes can come off their contacts with the respective target plugs while the stage is being moved, due to a creep phenomenon of piezo devices which are used for driving the probes in order to achieve a positioning resolution of 5 nm or less. From the reasons as mentioned above, it is optimal to rely on an image-shift operation to move the SEM field 410. An arrow 411 is displayed to clarify the direction in which one can find the probe 404 that is selected for driving. The direction in which the arrow is oriented varies depending on the direction in which a probe is driven.

In the example illustrated in FIG. 4C, an image-shift operation has been performed such that the probe 404 and target gate plug 408 can be observed within the SEM field 410. Current semiconductor devices have plugs, the size of which is 200 nm or less, while a magnification of the SEM for observation is approximately 10 k. With this magnification, an observation field extends approximately to 10 μm. For example, a current semiconductor memory mat has a sector width which is approximately 150 μm at most. If the sector width is made larger to increase the memory capacity, the response degrades due to high frequency components of the device, so that a larger capacity is accomplished by reducing the pitch of a plurality of plugs 409. The target gate plug 408 is located at the end of one side of the sector for pullup, and assuming that the remaining target plugs 402-405 which one wishes to inspect are located at the opposite end of the sector, the target plugs can be observed with the SEM over the entire range without moving the DUT stage as long as an image-shift moving amount of 150 μm or ±75 μm is satisfied. A conventional SEM may perform an image-shift operation after adjustments of electron optics elements to avoid observing possible contaminations which can stick to the elements during the adjustments of the electron optics elements when the SEM is set to an observation magnification of 50 k or higher for a resolution specimen (like good particles on carbon materials) or the like, and an image-shift moving amount should be approximately 15 µm at most in order to avoid a degradation in the resolution due to off-axis aberration associated with the image-shift operation, and particularly due to deflection chromatic aberration at a low accelerating voltage. Also, for purposes of avoiding observation of contaminations, coordinate positions need not be displayed after the image-shift operation.

However, the defect inspection apparatus lays out a SEM image and a CAD image, so that the defect inspection apparatus is required to have a function for allowing the CAD image to follow a change in the SEM image caused by an image-shift operation, and must have the ability to display an image-shift moving amount in coordinates because there can be a request to bring a probe into contact with a plug located at certain pitches away, even when the CAD image is not used. In the following, this coordinate display capabilities will be described with reference to FIGS. 5A, 5B, 5C.

FIG. 5A illustrates an example of an image-shift control GUI. DUT stage conversion coordinates 501 are coordinates of the DUT stage when an image-shift moving amount is converted to a DUT stage moving amount, and are transmitted to the CAD WS 117 or transmitted from the CAD WS 117. A CAD layout image has an area as wide as 10 mm×10 mm, so that even a movement over ±75 µm through an image-shift operation cannot accomplish a movement of the SEM image to fit to the entire CAD layout image through the image-shift operation. Also, a linear scale may be used for the DUT stage to accurately correspond a CAD layout image to the DUT stage coordinates. For this reason, the image-shift coordinates are converted to the DUT stage coordinates which are used for observations. Image-shift operational coordinates 502 are coordinates for representing an image-shift moving amount which is converted from coordinates at which the image-shift drives (image-shift DAC coordinates) to coordinates at which an operation (observation) is being actually under way, because a raster rotation function is operating for rotating the SEM image field, the image-shift operational coordinates 502 are required because they are different from the image-shift DAC coordinates. Since the SEM involves an objective lens rotating action, the raster rotation function is operated at all time to control such that a direction in which the DUT stage is moved matches a direction in which the SEM scans. When the user follows the pitch, the user references the image-shift operational coordinates. Details on the coordinate conversion will described later.

An RST 503 is a button for returning a shifted image to a midpoint. Any of hollow triangular arrow buttons 504, when clicked, causes an image to shift in a direction indicated by the clicked arrow button 504 by a moving amount selected in a combo-box 505. The user can enter a desired moving amount into the combo-box 505. A cross cursor 506 permits the user to visually know an actual coordinate position. Image-shift coordinates are displayed in coordinate boxes 507, or appropriate values may be directly entered into the coordinate boxes 507 to shift an image to a desired position. The function described herein is effective to coordinates selected by an option button.

FIG. 5B illustrates another example of the image-shift control GUI. The image-shift control GUI of FIG. 5B additionally comprises a pitch interval entry box 508, and counter boxes 509 for displaying the numbers of pitches in the X- and Y-directions, respectively, in addition to the functions shown in FIG. 5A. When the user enters a pitch into the entry box 508 and performs an image-shift operation, an integer part of the ratio of an image-shift moving amount to the pitch is displayed in the counter box 509 for each of the X- and Y-directions. Alternatively, when the user enters the number of pitches by which the user wishes to move an image, and performs an image-shift operation, a message 601 as shown in FIG. 6 is displayed in a message area 602 when a set number of counts (number of pitches) is reached. A click on a mouse in a Yes area 603 causes an image-shift operation to continue, whereas a click on a mouse in a No area 604 results in rejection of the image-shift operation. Since user always performs the image-shift operation for the SEM image field, the counter function is effective only when the image-shift operational coordinates are selected by the option button.

Figure 5C:
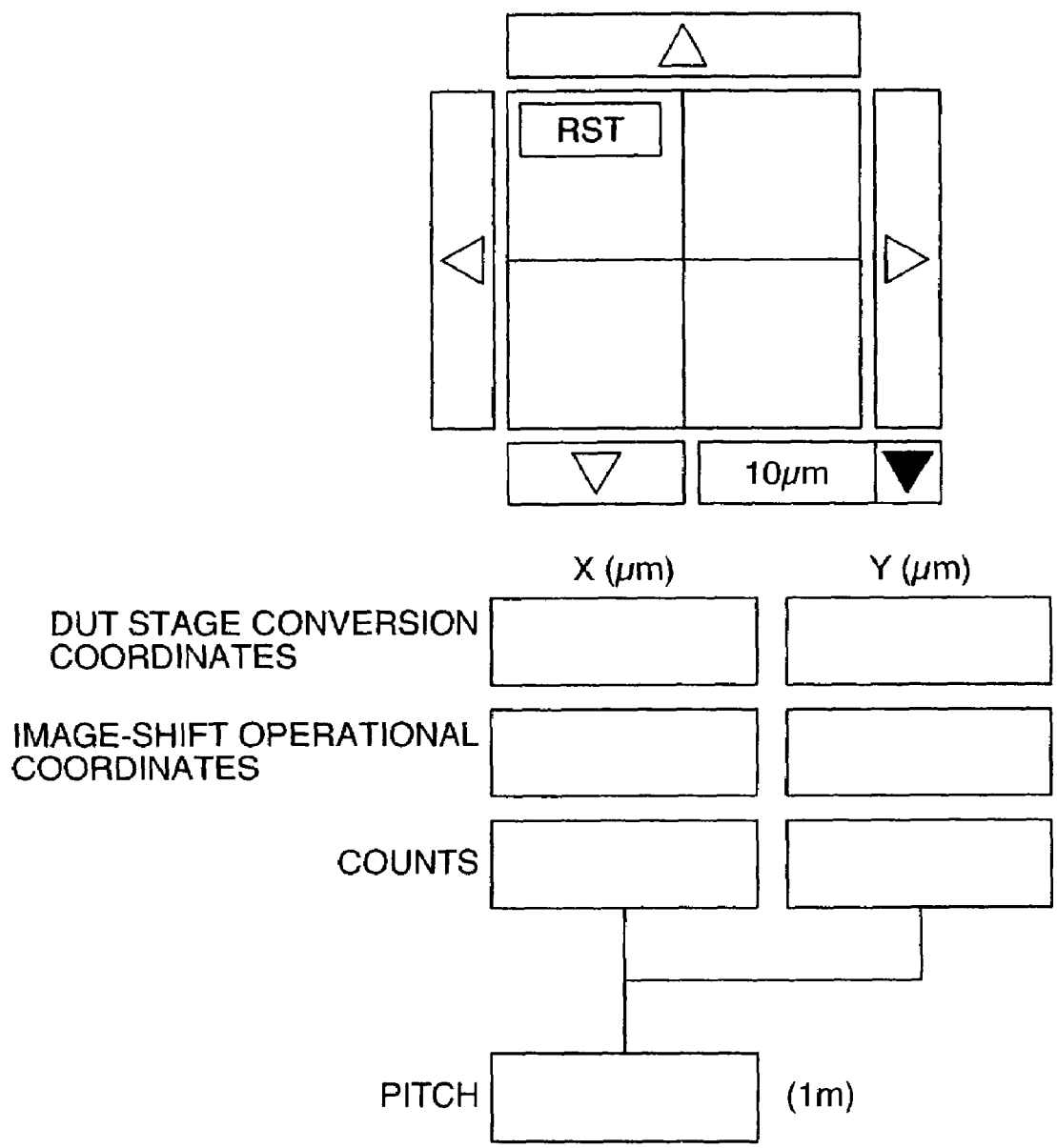

FIG. 5C is an example of the image-shift control GUI which limits the cross cursor, arrow-shaped buttons, combo-box, and counter function only to the image-shift operational coordinates, and displays the specimen conversion coordinates only as reference values. These limitations are placed because the user always operates on the image-shift operational coordinates, except for the entry of coordinates, the DUT stage conversion coordinates are meaningful when a communication is made with the CAD WS 117, and the processing is performed within the control computer 114.

Next, description will be made on a method of operating the defect inspection apparatus illustrated in FIG. 1 using the electron optics components illustrated in FIG. 2. Assume in the following description that positional information has already been calibrated for CAD image data and SEM image data. Details on a coordinate conversion method will be described later.

First, a method of calibrating positional information will be described in brief. The DUT stage is roughly moved to a position corresponding to a point on a certain pattern in a CAD image, and the DUT stage is finely adjusted, while observing on a SEM image, such that the same pattern appears at the center of the screen, to perform an alignment of CAD coordinates to the DUT stage coordinates at a first point. Next, the DUT stage is roughly moved to a position corresponding to a point on another pattern in the same CAD image, and the DUT stage is finely adjusted, while observing on the SEM image, such that the same pattern appears at the center of the screen, to perform an alignment of the CAD coordinates to the DUT stage coordinates at a second point. Finally, the DUT stage is roughly moved to a position corresponding to a point on a further pattern on the same CAD image, and the DUT stage is finely adjusted, while observing on the SEM image, such that the same pattern appears at the center of the screen to perform an alignment of the CAD coordinates to the DUT stage coordinates at a third point. The foregoing operations permit a correspondence to be established between the CAD coordinates and DUT stage coordinates. During the alignment operation, the SEM-based observation may be performed at a low magnification of 100 or lower when the DUT stage is roughly moved, and at a high magnification of approximately 10 k when the DUT stage is finely adjusted. The alignments are preferably performed at three points near corners of the specimen in order to increase the accuracy of the conversion from the CAD coordinates to the DUT stage coordinates over the entire specimen.

Figure 7B:
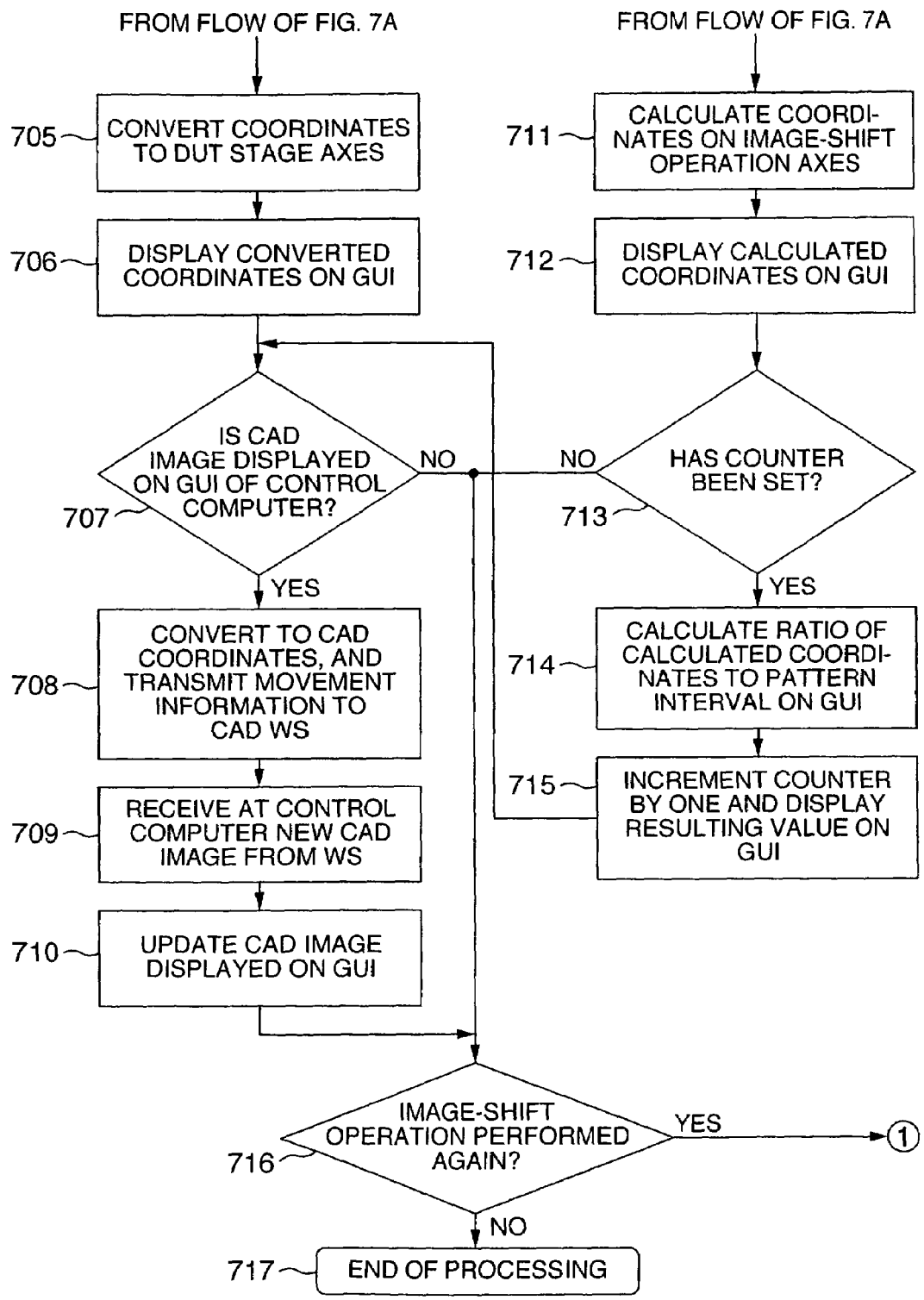

Referring first to FIGS. 7A, 7B, description will be made on an image-shift operation made by the user through the GUI of the PC 119, or with associated knobs and joystick of the control panel 120.

As the user performs an image-shift operation through the GUI of the SEM control PC 119 or with associated knobs and joystick of the control panel 120 (step 701), an operating amount is transmitted to the control computer 114 which calculates a DAC changing amount for an image-shift XY. The control computer 114 also calculates a DAC amount of the image-shift XY from a coordinate input amount (step 702). For the DAC changing amount, the control computer 114 adds the DAC changing amount to a current DAC amount or subtract the DAC changing amount from the current DAC amount. Once the DAC amount is determined, the image-shift is actually performed through the electron optics control means 116 (step 703). Also, the control computer 114 calculates the coordinates on the image-shift DAC axes from an actually set image-shift DAC value (step 704).

Subsequently, two different sequence of steps may be contemplated. A first sequence of steps converts the image-shift DAC coordinates to the DUT stage coordinates, and a second sequence of steps converts the image-shift DAC coordinates to the image-shift operation axes. First described is the sequence of steps for converting the image-shift DAC coordinates to the DUT stage coordinates.

The control computer 114 converts the image-shift DAC coordinates to the DUT stage coordinates (step 705). The converted coordinate values are transmitted to the SEM control PC 119 for displaying the coordinates on the GUI (step 706). In this event, when the CAD WS 117 is not linked to the SEM control PC 119 so that a CAD layout image is not overlaid on a SEM image (step 707), it is determined again whether or not an image-shift operation occurs (step 716).

Conversely, when the CAD WS 117 is linked to the SEM control PC 119 so that the CAD layout image is overlaid on the SEM image (step 707), the control computer 114 converts the DUT stage coordinates to CAD coordinates and transmits a moving amount to the CAD WS 117 (step 708) before it receives a new CAD image from the CAD WS 117 (step 709), and overlays the CAD image on the GUI of the SEM control PC 119 (step 710). Subsequently, the flow proceeds to step 707. It is determined again whether or not an image-shift operation occurs (step 716), and the processing is terminated when no image-shift operation occurs (step 716), or the flow returns to step 702 when the image-shift operation occurs (step 716), such that the control computer 114 again performs similar processing to the foregoing.

Next described is the sequence of steps for converting the image-shift DAC coordinates to the image-shift operation axes. The control computer 114 converts the image-shift DAC coordinates to the image-shift operational coordinates (step 711). Then, the control computer 114 transmits the converted coordinate values to the SEM control PC 119 for displaying the coordinates on the GUI (step 711).

The control computer 114 determines whether or not the counters have been set on the image-shift operational coordinate axes on the SEM control PC 119 for displaying the number of pattern widths by which a movement has been made in the X- and Y-directions, respectively. When the counters are not set (step 713), the flow proceeds to step 707. Conversely, when the counters have been set (step 713), the control computer 114 calculates the ratio of each of the calculated image-shift operational coordinates to the pattern width selected on the GUI of the SEM control PC 119, removes the decimal point from the calculated ratio, and defines the resultant value as a count value in the X- or Y-direction (step 714). The control computer 114 transmits the count values to the SEM control PC 119 for display on the GUI (step 715). Subsequently, the flow proceeds to step 707.

Also, the SEM control PC 119 sets the number of pattern widths by which a movement is made in each of the X- and Y-directions, or the SEM control PC 119 sets an image-shift amount by which a movement is made on each of the image-shift operational coordinate axes, and the control computer 114 compares actual count values with the set values. When the set values are exceeded by the actual count values, the image of FIG. 6 is displayed for permitting the user to determine whether or not the image-shift operation is continued.

Figure 8:
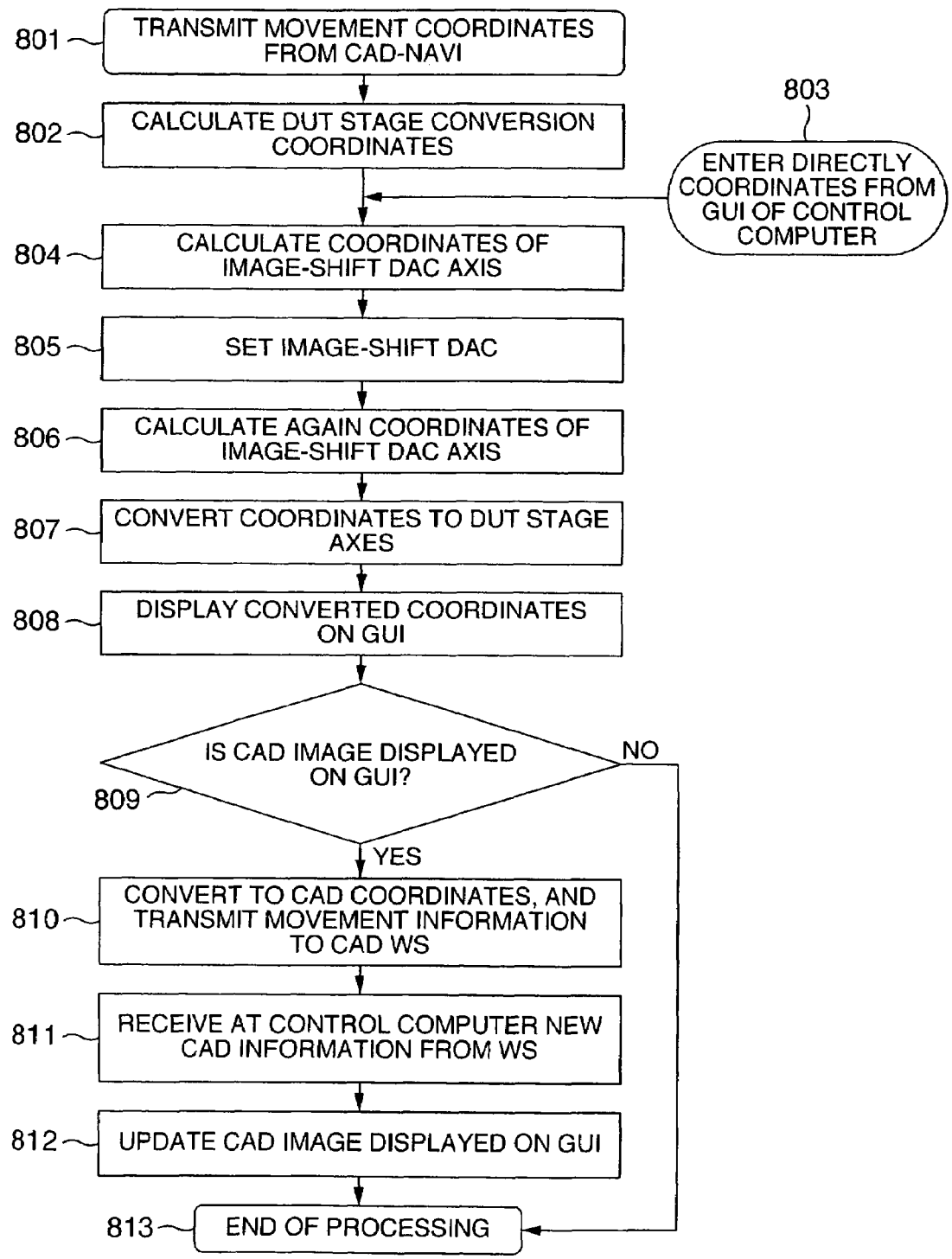
FIG. 8 is a flow chart illustrating a basic flow of image-shift control in the defect inspection apparatus illustrated in FIG. 1.

Referring next to FIG. 8, description will be made on the image-shift operation when the user moves a layout pattern on the CAD WS 117.

A moving amount by which a layout pattern has been moved on the CAD WS 117 is transmitted to the control computer 114 (step 801). The control computer 114 calculates a moving amount on the image-shift coordinates, as converted to the DUT stage axes (step 802). When the specimen conversion coordinates are directly inputted on the GUI of the SEM control PC 119, the control is started from this moment (step 803). Next, the moving amount is transmitted to the control computer 114 which calculates a moving amount on the image-shift DAC axes. The control computer 114 also calculates input coordinate values on the image-shift DAC axes from the input coordinate amounts (step 804). Next, the control computer 114 calculates a DAC change amount from the moving amount, and adds the calculated DAC change amount to a current DAC amount or subtracts the DAC change amount from the current DAC amount. The control computer 114 calculates the DAC amount from the input coordinate values. Once the DAC amount is determined, an image-shift is actually performed through the electron optics control means 116 (step 805). Also, the control computer 114 again calculates the coordinates on the image-shift DAC axes from the actually set image-shift DAC value (step 806).

The control computer 114 converts the image-shift DAC coordinates to the DUT stage coordinates (step 807). The converted coordinate values are transmitted to the SEM control PC 119 for displaying the coordinates on the GUI (step 808). In this event, when the CAD WS 117 is not linked to the SEM control PC 119, so that the CAD layout image is not overlaid on the SEM image (step 809), the processing is terminated (step 813).

Conversely, when the CAD WS 117 is linked to the SEM control PC 119, so that the CAD layout image is overlaid on the SEM image (step 809), the control computer 114 converts the DUT stage coordinates to the CAD coordinates and transmits a moving amount to the CAD WS 117 (step 810) before it receives a new CAD image from the CAD WS 117 (step 811), and overlays the CAD image on the GUI of the SEM control PC 119 (step 812), followed by termination of the processing (step 813).

By executing the foregoing steps, a CAD image and coordinates overlaid on the GUI of the SEM control PC 119 can be automatically updated following a change in the SEM image field resulting from an image-shift operation, thus significantly reducing a burden on the user during the probing.

Next, description will be made on the coordinate conversion associated with the image-shift described in the foregoing embodiment. The following six sets of coordinates should be taken into consideration in the image-shift control:

(1) DUT stage coordinates ($x_{DUT}$, $y_{DUT}$);
(2) Image-shift coordinates converted to DUT stage ($x_{IS\text{-}DUT}$, $y_{IS\text{-}DUT}$);
(3) Image-shift axis correction coordinates ($x_{IS}$, $y_{IS}$);

(4) Ideal image-shift coordinates ($x_{IS}$, $y_{IS}$);

(5) Image-shift DAC coordinates ($x_{IS-DAC}$, $y_{IS-DAC}$); and (6) Image-shift operational coordinates ($x_{IS-OP}$, $y_{IS-OP}$).

The DUT stage coordinates (1) and image-shift coordinates converted to the DUT stage (2) are basically completely the same coordinates if the linearity and orthogonality can be ignored for the DUT stage. The image-shift axis correction coordinates (3) are coordinates converted when an image-shift coil is ideally disposed. The ideal image-shift coordinates (4) are similar to the image-shift axis correction coordinates (3), and are coordinates which are converted in consideration of a field offset which occurs when an off-axis due to an image-shift is corrected. The image-shift DAC coordinates (5) are coordinates converted when the orthogonality of the image-shift coil deviates from an ideal axis in the ideal image-shift coordinates (4). The image-shift operational coordinates (6) are coordinates converted to fit the coordinate axes of the image-shift axis correction coordinates (3) to the SEM scan axis, and are used for correcting the rotation of the scan axis caused by excitation of the objective lens to the coordinate axes of the DUT stage, and for electrically rotating the scan axis.

Figure 9:
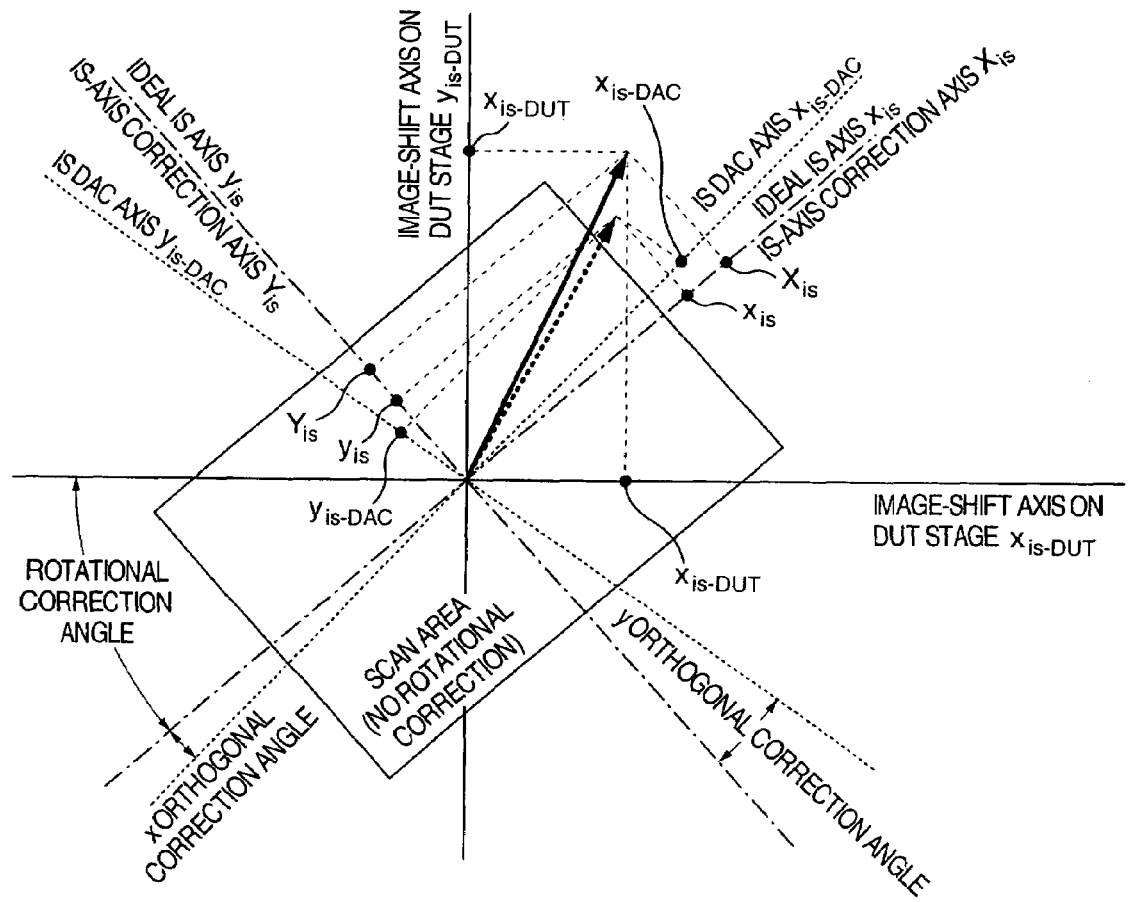
FIG. 9 is a conceptual diagram representing the relationship between DUT stage coordinates and image-shift DAC coordinates.
Figure 10:
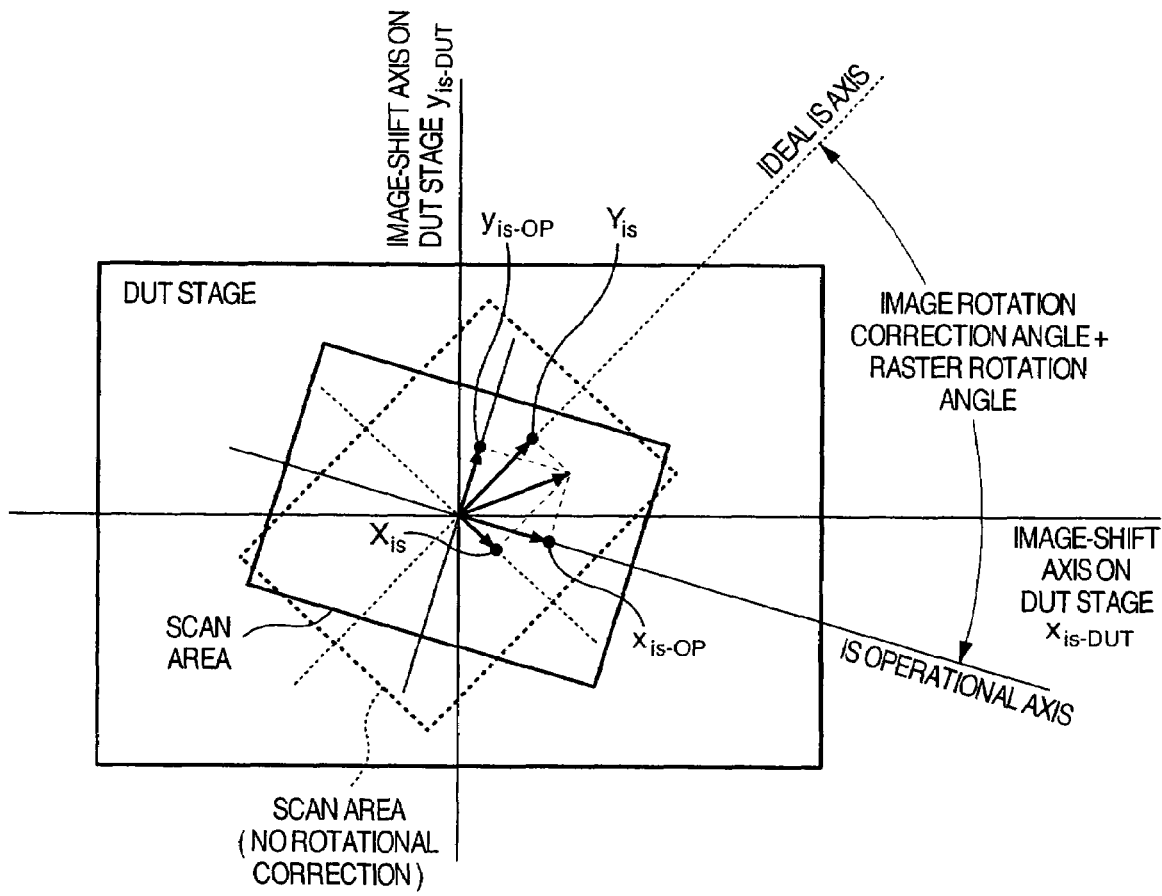
FIG. 10 is a conceptual diagram representing the relationship between image-shift operational coordinates and image-shift DAC coordinates.

As described in connection with FIGS. 7A, 7B, 8, conversion in coordinates required for controlling an image-shift operation involve the relationships of a conversion between the coordinates ($x_{IS-DUT}$, $y_{IS-DUT}$) (2) and the coordinates ($x_{IS-DAC}$, $y_{IS-DAC}$) (5) and a conversion between the coordinates ($x_{IS-OP}$, $y_{IS-OP}$) (6) and the coordinates ($x_{IS-DAC}$, $y_{IS-DAC}$) (5) The respective relationships of the coordinate conversions are described in FIGS. 9 and 10, respectively. The respective coordinate conversions can be expressed in mathematical formulae as follows:

$$\begin{pmatrix} x_{IS-DUT} \\ y_{IS-DUT} \end{pmatrix} = A \begin{pmatrix} X_{IS} \\ Y_{IS} \end{pmatrix}$$
$$\begin{pmatrix} X_{IS} \\ Y_{IS} \end{pmatrix} = B \begin{pmatrix} x_{IS} \\ y_{IS} \end{pmatrix}$$
$$\begin{pmatrix} x_{IS} \\ y_{IS} \end{pmatrix} = C \begin{pmatrix} x_{IS-DAC} \\ y_{IS-DAC} \end{pmatrix}$$
$$\begin{pmatrix} x_{IS-OP} \\ y_{IS-OP} \end{pmatrix} = D \begin{pmatrix} X_{IS} \\ Y_{IS} \end{pmatrix}$$

Equations 1

A matrix A is a matrix of linear transformation of the image-shift coordinates converted to the DUT stage and the image-shift axis correction coordinates, and depends on a rotating angle due to excitation of the objective lens. A matrix B is a matrix of linear transformation of the image-shift axis correction coordinates and ideal image-shift coordinates, and is a matrix which takes into consideration a field offset which occurs when an off-axis during an image-shift operation is corrected by a single alignment coil or image-shift coil. A matrix C is a matrix of linear transformation of the ideal image-shift coordinates and image-shift DAC coordinates, and depends on an orthogonality angle of the image-shift coil. A matrix D is a matrix of linear transformation of the image-shift operational coordinates and image-shift axis correction coordinates, and depends on an electric rotating angle of the scan axis due to raster rotation in addition to a rotating angle due to excitation of the objective lens. When the image-shift axis can also be rotated, the matrix D depends on a mechanical offset angle of the scan axis from the ideal image-shift axis.

From the foregoing relationships, transformations can be derived for (2) and (5) and for (6) and (5).

$$\begin{pmatrix} x_{IS-DUT} \\ y_{IS-DUT} \end{pmatrix} = ABC \begin{pmatrix} x_{IS-DAC} \\ y_{IS-DAC} \end{pmatrix}$$
$$\begin{pmatrix} x_{IS-DAC} \\ y_{IS-DAC} \end{pmatrix} = (ABC)^{-1} \begin{pmatrix} x_{IS-DUT} \\ y_{IS-DUT} \end{pmatrix}$$

Equations 2

$$\begin{pmatrix} x_{IS-OP} \\ y_{IS-OP} \end{pmatrix} = DBC \begin{pmatrix} x_{IS-DAC} \\ y_{IS-DAC} \end{pmatrix}$$
$$\begin{pmatrix} x_{IS-DAC} \\ y_{IS-DAC} \end{pmatrix} = (DBC)^{-1} \begin{pmatrix} x_{IS-OP} \\ y_{IS-OP} \end{pmatrix}$$

Equation 3

Some aspects to be noted for each of matrix elements will be described below.

The actual DUT stage coordinates and the image-shift coordinates converted to the DUT stage may suffer from a zero offset depending on the linearity and orthogonality of the DUT stage and the positioning of the secondary electron detector of the SEM, and can therefore fail to fit to each other. In such a case, the zero offset can be corrected for by the following relationship:

$$\begin{pmatrix} x_{DUT} \\ y_{DUT} \end{pmatrix} = A' \begin{pmatrix} x_{IS-DUT} \\ y_{IS-DUT} \end{pmatrix} + \begin{pmatrix} \Delta x_{IS-DT} \\ \Delta y_{IS-DUT} \end{pmatrix}$$

Equation 4

A matrix A' is a matrix of linear transformation which takes into consideration the linearity and orthogonality of the DUT stage. $\Delta x_{IS-DUT}$, $\Delta y_{IS-DUT}$ represent offset amounts of the DUT stage from a spot irradiated with a primary electron beam. In an actual apparatus, a relative movement from fixed conditions is often relied on to handle the offset amounts. Also, in an image-shift operation in a range of approximately ±75 µm as compared with a wide operation range of the DUT stage extending 10 mm or more, the linearity and orthogonality of the DUT stage can be often ignored. Therefore, the matrices A and A' are treated as the same coordinates in the following description.

The matrices B, C comprise elements which are not prominent in a normal image-shift range of ±15 µm, as described in connection with FIGS. 4A, 4B, 4C, but are prominent when an image-shift range of ±75 µm or more is accomplished, as required by the defect inspection apparatus, and which must be taken into consideration for highly accurate positional control. The matrix B can be equal with a unit matrix when a correction is added to prevent the object point of the objective lens from being moved by two alignment coils or an image-shift coil. In the following, the matrix B will be described with reference to FIGS. 11A, 11B.

Figure 11A:
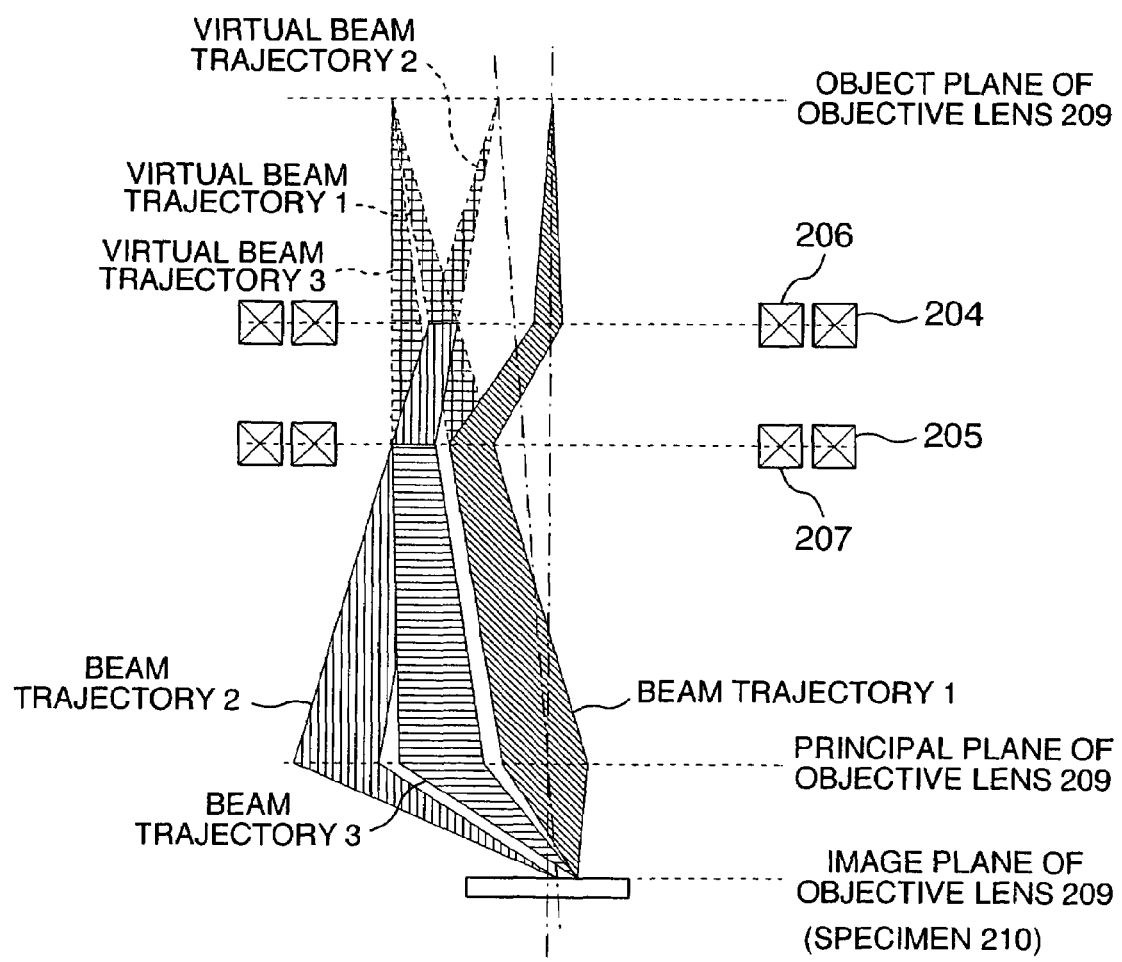
FIGS. 11A and 11B are conceptual diagrams for describing a field offset associated with an image-shift axis correction.

FIG. 11A conceptually illustrates a ray trajectory during the image-shift control. An actual trajectory of a primary electron beam is represented by a ray trajectory 1. When image-shift coils 204, 205 are driven, the ray trajectory 1 changes to a virtual ray trajectory 1. When an upper alignment coil 206 alone is further driven, the ray trajectory 1 changes to a combination of a virtual ray trajectory 2 and a ray trajectory 2. When a lower alignment coil 207 is further driven, the ray trajectory 1 changes to a combination of a virtual ray trajectory 3 and a beam trajectory 3.

Figure 11B:
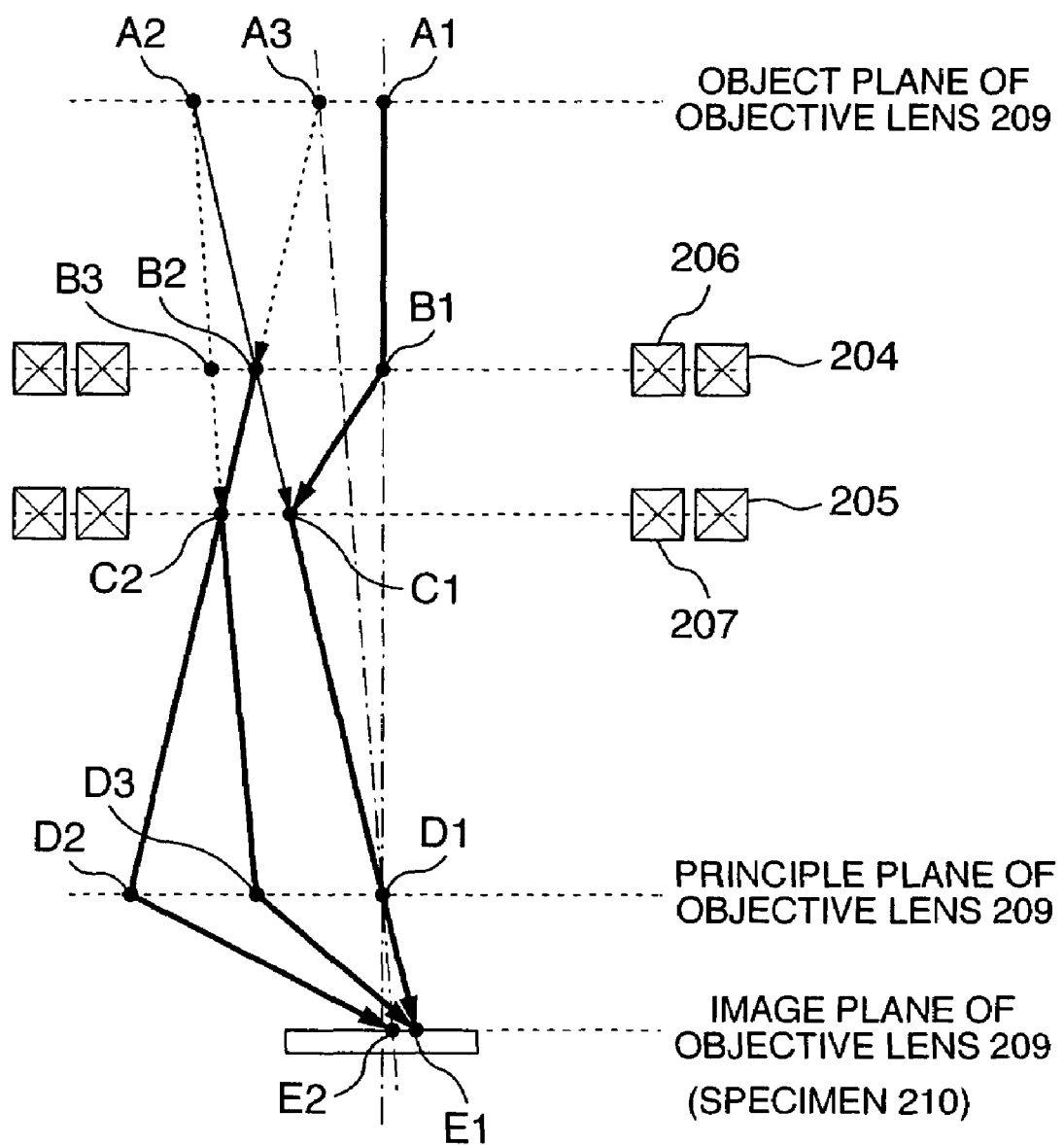

FIG. 11B only illustrates central trajectories of the ray trajectories shown in FIG. 11A. The primary electron beam, emitted from a primary electron beam crossover point (object point A1 of the objective lens) on the surface of the objective lens, is deflected by the upper image-shift coil 204 (B1), is again deflected by the lower image-shift coil 205 in the opposite direction (C1), passes through one point (D1) on the main surface of the objective lens, and is irradiated obliquely to an objective lens image point (E1) on an objective lens image plane (i.e., the specimen). As the image-shift coils are driven, the object point A1 of the objective lens is shifted to A2, so that the trajectory virtually follows A2-B2-C1-D1-E1. When the upper alignment coil 206 alone is driven in this state, the object point A2 of the objective lens is shifted to A3, so that the trajectory changes to A3-B2-C2-D2-E2. The shift of the object point A2 of the objective lens to A3 causes a shift of the objective lens image point E1 to E2, so that the primary electron beam is irradiated to an offset spot. Further, when the lower alignment coil 207 is also driven in this state to shift the object point A3 of the objective lens to fit to A3, the resulting trajectory follows A2-B2-C2-D3-E1. When the object point A3 of the objective lens is fitted to A2, the primary electron beam is irradiated to the original objective lens image point E1, so that the offset of the irradiated spot can be removed.

The image-shift in SEM is basically relied on a method of moving a spot on a specimen irradiated with a primary electron beam by deflecting the primary electron beam using two image-shift coils. When the primary electron beam is deflected by an image-shift coil, the primary electron beam obliquely impinges on a specimen, resulting in off-axis aberration. Also, chromatic aberration is produced in association with the deflection. For minimizing the influence of such aberrations, the image-shift control is conducted such that a desired axis is found by adjusting the ratio of currents applied to the upper and lower image-shift coils, or currents independently applied to the respective coils in the X-direction and Y-direction, respectively. Actually, however, the desired axis cannot be found only with adjustments in the same direction by a rotating action of the objective lens. For this reason, a single alignment coil may be provided independently of the image-shift coils, or an alignment signal is superimposed on the upper image-shift coil to add a correction depending on an image-shift amount, thereby achieving the identification of the desired axis.

As described above, a correction made by a single alignment coil causes a shift of the object point of the objective lens and a resulting shift of a spot on a specimen irradiated with the primary electron beam to give rise to a field displacement, thus resulting in coordinates which are different from those to which one wishes to actually shift the primary electron beam. In consideration of this amount, the matrix B is set in order to shift the primary electron beam to desired image-shift coordinates. However, it is possible to avoid the primary electron beam shifted from an intended irradiated spot on the specimen and remove the field movement by adding a correction depending on an image-shift amount to an alignment signal by providing two independent alignment coils or superimposing the alignment signal on the upper and lower image-shift coils to find the desired axis, and simultaneously conducting the image-shift control to prevent the object point of the objective lens from shifting. When the field movement can be removed by this method, the matrix A can be treated as a unit matrix, without the need for taking into consideration the matrix B, resulting in an improvement in the coordinate conversion accuracy.

The desired axis, herein referred to, may be exemplified by a current center axis. The current center axis refers to an axis on which a change in excitation of an objective lens does not cause a change in the position of the image point of the objective lens. Among the off-axis aberrations, astigmatism can be corrected by an astigmatism correcting coil, not shown in FIG. 2, while field curvature aberration can be corrected by adjusting the excitation of the objective lens. Though depending on the characteristics of a particular objective lens and electron optics conditions, an image-shift of 100 μm will cause coma aberration of approximately 2-3 nm to leave on the current center axis. However, it is chromatic aberration resulting from the image-shift, which exerts larger influences. Specifically, the chromatic aberration is prominent particularly at low accelerating voltages equal to or lower than 5 kV. For example, in a charged particle beam apparatus which is equipped with a field emission electron source having an energy spread of 0.3 eV, an image-shift of 100 μm at an accelerating voltage of 2 kV causes chromatic aberration of approximately 14 nm. Particularly, in the defect inspection apparatus which is intended for semiconductor materials as specimen, observations at low accelerating voltages are essential in order to minimize damages to specimen. Thus, an axis, called the "achromatic axis," which can remove off-axis chromatic aberration and deflection chromatic aberration of an objective lens, can be assumed as a desired axis. The aberrations given herein as examples differ from one charged particle beam apparatus to another, as will be apparent to users of charged particle beam apparatuses.

For conditions to find a desired axis, the current center axis is generally well known in charged particle beam apparatuses. In the following, the achromatic axis will be described in detail with reference to appropriate equations.

$$w_0 = a \cdot w'_0 \qquad \text{Equation 5}$$

where wo, wo' are the position and inclination of the primary electron beam on the surface of the objective lens, and $\underline{a}$ represents conditions for a desired axis. The position wi and inclination wi' of the primary electron beam on the image plane of the objective lens can be expressed by the following equations using Equation 5:

$$w_i = a \cdot g_i \cdot w'_0$$

$$w'_i = (a \cdot g'_i + h'_i) \cdot w'_0 \qquad \text{Equations 6}$$

where gi, hi, gi', hi' are the positions and inclinations at the image points of two paraxial rays well known in the charged particle theory. In the charged particle theory, chromatic aberration of a primary electron beam obliquely incident on an objective lens is expressed by the following equation:

$$\Delta w_c = \{C_{c0} \cdot w'_i + (C_{cm} + jC_{cr}) \cdot w_i\} \cdot \left(\frac{\Delta V}{V}\right) \qquad \text{Equation 7}$$

where Cco is an axial chromatic aberration coefficient, Ccm is a magnification chromatic aberration coefficient, Ccr is an anisotropic chromatic aberration coefficient, V is the energy of the primary electron beam on the objective lens image plane, and ΔV is variations in the energy of the primary electron beam. An image-shift causes variations ΔV in the energy which result in variations in the position to which the primary electron beam propagates. The variations can be regarded as a type of aberration, which is called the "deflection chromatic aberration." This deflection chromatic aberration is not included in Equation 7. For example, in a charged particle beam apparatus equipped with a field emission electron source having an energy width of 0.3 eV, an image-shift of 100 μm at an accelerating voltage of 2 kV causes deflection chromatic aberration of approximately 8 nm, as compared with the chromatic aberration expressed by Equation 7 which is approximately 6 nm. While it is possible to find from Equation 7 axial conditions under which the chromatic aberration disappears, deflection chromatic aberration of 8 nm remains in the foregoing example. It is therefore necessary to find an axis $\underline{a}$ which satisfies conditions under which the chromatic aberration is eliminated, in consideration of the deflection chromatic aberration as well. The chromatic aberration produced by a deflecting action such as the image-shift can be expressed by the following equation:

$$\Delta w_{def} = C_{def} \cdot r_{IS} \cdot \left(\frac{\Delta V}{V}\right) = C_{def} \cdot a \cdot g_i \cdot w_0' \cdot \left(\frac{\Delta V}{V}\right) \qquad \text{Equation 8}$$

where:

$$C_{def}(\text{MAGNETIC FIELD}) = -\frac{1}{2} \cdot \left(\frac{V}{V_{def}}\right) \qquad \text{Equations 9}$$

$$C_{def}(\text{ELECTRO}-\text{STATIC FIELD}) = -\left(\frac{V}{V_{def}}\right)$$

where $C_{def}$ is a chromatic aberration coefficient due to deflection, and takes different values for magnetic deflection and electro-static deflection, ris is an image-shift operation amount, and Vdef is the energy of the primary electron beam at a deflected location. Combining Equation 9 with Equation 10 results in the following equation:

$$\Delta w_c = \{C_{c0} \cdot (a \cdot g_i' + h_i') + (C_{cm} + jC_{cr}) \cdot a \cdot g_i + C_{def} \cdot a \cdot g_i\} \cdot \qquad \text{Equation 10}$$

$$w_0' \cdot \left(\frac{\Delta V}{V}\right)$$

The axis $\underline{a}$ which satisfies the condition for deriving zero from Equation 10 is the achromatic axis which can be expressed by the following equation:

$$a = -\frac{C_{c0} \cdot h_i'}{C_{c0} \cdot g_i' + (C_{cm} + C_{def}) \cdot g_i + jC_{cr} \cdot g_i} \qquad \text{Equation 11}$$

Among the equations described above, wo, wo', wi, wi', $\underline{a}$, rIS take complex numbers, while the remainings take real numbers. Also, the exemplary values given above differ depending on the characteristics of the objective lens.

As previously described, a correction depending on an image-shift amount is added to an alignment signal to create an achromatic axis by providing two independent alignment coils or superimposing an alignment signal on the upper and lower image-shift coils, and simultaneously, control is conducted to prevent the object point of the objective lens from shifting, thereby making it possible to avoid the primary electron beam irradiated to a shifted position on a specimen and effectively eliminate the chromatic aberration.

Published Japanese Translation of PCT International Publication for Patent Application WO 01/033603 describes an ExB field generator, i.e., an apparatus which generates an energy distribution, which has the same magnitude as and a direction reverse to off-axis/deflection chromatic aberration corresponding to an image-shift amount, using a wien filter to cancel out aberration. The use of this strategy will result in the realization of a current center axis of the objective lens to reduce off-axis aberration such as coma aberration and an additional reduction in off-axis/deflection chromatic aberrations. Presumably, the use of the ExB field generator may involve a complicated configuration and control of the apparatus and a high cost.

Finally, description will be made on coordinate conversion used in communications between the SEM control PC 119 and CAD WS 117. Coordinates which should be taken into consideration in the CAD navigation include the following four sets:

(1) DUT stage coordinates ($x_{DUT}$, $y_{DUT}$)
(2) Base stage coordinates ($x_{BASE}$, $y_{BBASE}$)
(3) Image-shift coordinates converted to DUT stage ($x_{IS-DUT}$, $y_{IS-DUT}$); and
(4) CAD navigation coordinates ($x_{CAD}$, $y_{CAD}$)

The CAD navigation coordinates (4) define layout coordinates for a CAD image which has an ideal magnification and pattern information. The DUT stage coordinates (1) represent a linear scale value of the DUT stage. However, the coordinates also include an correction term for small errors due to backlash of stage mechanisms and the like. The base stage coordinates (3) are coordinates resulting from a conversion from an image-shift amount to the DUT stage axis. The coordinate conversion is performed according to the following equation:

$$\begin{pmatrix} x_{CAD} \\ y_{CAD} \end{pmatrix} = \begin{pmatrix} x_{DUT} \\ y_{DUT} \end{pmatrix} + \begin{pmatrix} x_{BASE} \\ y_{BASE} \end{pmatrix} + \begin{pmatrix} x_{IS-DUT} \\ y_{IS-DUT} \end{pmatrix} \qquad \text{Equation 12}$$

When the DUT stage and base stage imply rotational misalignment and zero offset, a conversion correction may be made in a manner similar to Equation 4.

While the foregoing embodiment has been described in connection with a scanning electron microscope which is given as an example of a charged particle beam apparatus, it will be apparent to developers and users of charged particle beam apparatuses that the same description can be applied to a focused ion beam apparatus for observing and processing specimen using ion beams. Also, due to the use of heavy elements such as Ga ions, an electrostatic lens is used for the objective lens instead of a magnetic lens. Thus, the matrix A in Equation 1 need not be taken into consideration because there is no rotating action, as experienced with a magnetic objective lens. Also, since the rotating action of the objective lens can also be ignored in the matrix D as is the case with the matrix A, it can be readily contemplated that the image-shift control accuracy is improved.

The present invention proposes a charged particle beam apparatus which can control an image-shift of ±75 μm or more without a degraded resolution due to chromatic aberration, and can display and input coordinates by a conversion from the stage coordinates to the image-shift control coordinates, a conversion from the image-shift operational coordinates to the image-shift control coordinates, and the realization of the achromatic axis. The present invention also proposes an image-shift control method suitable for the introduction of CAD navigation into a defect inspection apparatus which is a combination of a probe with the charged particle beam apparatus. According to the present invention, the user's convenience is remarkably improved when the user uses an image-shift function of the charged particle beam apparatus and defect inspection apparatus.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. In an inspection apparatus for measuring electrical properties of a specimen having a fine circuit line pattern a charged particle beam apparatus comprising:
   a plurality of probes configured to be brought into contact with the circuit line pattern to measure electric properties of the specimen;
   device for irradiating the specimen with a charged particle beam;
   image-shift device for moving a spot irradiated with the charged particle beam on the specimen;
   device for detecting a secondary charged particle beam generated from the specimen by irradiating the specimen with the charged particle beam to capture an image of the specimen;
   display device for displaying the image;
   input device for specifying an arbitrary location on the image;
   storing device for storing information on the circuit line pattern;
   image processing device for processing the captured image for displaying the image on said display device; and
   communication device for interconnecting said storing device and said image processing device,
   wherein said defect inspection apparatus displays the circuit line pattern and the captured image on said display device, displays information for requesting a user to specify the same location on the circuit line pattern and on the captured image, and communicates information on coordinates of a specified position between said storing device and said image processing device, and the coordinate information includes positional information of the charged particle beam on the specimen by said image-shift device.

2. A charge particle beam apparatus according to claim 1, wherein:
   said image-shift device is capable of moving a spot irradiated with the charged particle beam by 150 µm or more or by ±75 µm or more.

3. A charged particle beam apparatus according to claim 1, wherein:
   said display device displays both the captured image and the circuit line pattern.

4. A charged particle beam apparatus according to claim 3, wherein:
   said display device displays the captured image and the circuit line pattern in a superimposed manner.

5. A charged particle beam apparatus according to claim 1, wherein:
   said display device includes device for selecting DUT stage coordinates converted into a DUT stage, and image-shift operational coordinates converted from the image-shift moving amount into an image rotating direction in which an observation is being made.

6. A charged particle beam apparatus according to claim 5, wherein:
   said display device includes device for selecting an image-shift moving amount and a moving direction from previously preset candidates, and shifting the charged particle beam to the selected converted coordinates.

7. A charged particle beam apparatus according to claim 5, wherein:
   said display device includes device for inputting and displaying the selected converted coordinates, and
   said charged particle beam apparatus further comprises device for shifting the charge particle beam to an arbitrary position on the selected converted coordinates by directly inputting coordinates.

8. A charged particle beam apparatus according to claim 1, wherein:
   said display device includes device for simultaneously displaying the DUT stage coordinates and the image-shift operational coordinates.

9. A charged particle beam apparatus according to claim 8, wherein:
   said display device includes device for selecting an image-shift moving amount and a moving direction from previously preset candidates, and shifting the charged particle beam to the image-shift operational coordinates.

10. A charged particle beam apparatus according to claim 8, wherein:
    said display device includes device for inputting and displaying the selected converted coordinates, and
    said charged particle beam apparatus further comprises device for shifting the charge particle beam to an arbitrary position on the selected converted coordinates by directly inputting coordinates.

11. A charged particle beam apparatus according to claim 1, wherein said display device includes:
    device for inputting a pitch for the circuit line pattern, and
    counter device for displaying an integer part of a ratio of the image-shift moving amount to the pitch.

12. A charged particle beam apparatus according to claim 11, further comprising:
    device for inputting a count value to said counter device; and
    device for displaying a message on said display device when the integer part of the ratio of the image-shift moving amount to the pitch reaches an inputted count value.

13. A charged particle beam apparatus according to claim 1, further comprising:
    a charged particle beam source for emitting a charged particle beam;
    a condenser lens for focusing the charged particle beam;
    an objective lens for focusing the focused charged particle beam on the surface of the specimen;
    a deflector for scanning the charged particle beam on the specimen;
    two image-shift deflectors;
    an optical axis control deflector; and
    device for adjusting deflection signals applied to said two image-shift deflectors independently of each other or adjusting the ratio of one deflection signal to the other to move the spot on the specimen irradiated with the charged particle beam, and adjusting a deflection signal applied to said one optical axis control deflector to deflect a center axis of the charged particle beam, i.e., an optical axis to realize an objective lens axis which is capable of effectively eliminating chromatic aberration produced when the charged particle beam is directed obliquely into said objective lens by said image-shift deflectors, and chromatic aberration produced by the image-shift deflection.

14. A charged particle beam apparatus according to claim 13, further comprising:
   device for superimposing the deflection signal applied to said one optical axis control deflector on the deflection signal applied to the upper or the lower one of said two image-shift deflectors.

15. A charged particle beam apparatus according to claim 13, wherein:
   said optical axis control deflector comprises two optical axis control deflectors, and
   said charged particle beam apparatus further comprises device for adjusting deflection signals applied to said two optical axis control deflectors independently of each other or adjusting the ratio of one deflection signal to the other to fix the object point of said objective lens.

16. A charged particle beam apparatus according to claim 15, further comprising:
   device for superimposing the deflection signals applied to said two optical axis control deflectors on said two image-shift deflectors.

17. A charged particle beam apparatus according to claim 1, wherein said specimen is a wafer.

18. A charged particle beam apparatus according to claim 1, wherein said specimen is a part of a wafer.

* * * * *